US007001760B2

(12) United States Patent
Ryu et al.

(10) Patent No.: US 7,001,760 B2
(45) Date of Patent: Feb. 21, 2006

(54) HEPATITIS B VIRUS VECTORS FOR GENE THERAPY

(75) Inventors: Wang-Shick Ryu, Seoul (KR); Jehan Lee, Goyang-shi (KR); Jong Keun Jeong, Seoul (KR); Woo Young Cho, Seoul (KR); Gye Soon Yoon, Sungnam-shi (KR)

(73) Assignee: Wang-Schick Ryu (KR)

( * ) Notice: Subject to any disclaimer, the term of this patent is extended or adjusted under 35 U.S.C. 154(b) by 862 days.

(21) Appl. No.: 09/837,297

(22) Filed: Apr. 19, 2001

(65) Prior Publication Data

US 2001/0049145 A1 Dec. 6, 2001

(30) Foreign Application Priority Data

Apr. 20, 2000 (KR) ........................................ 2000-21070
Apr. 12, 2001 (KR) ........................................ 2001-19645

(51) Int. Cl.
*C12N 15/00* (2006.01)
*C12N 15/51* (2006.01)

(52) U.S. Cl. .................. 435/320.1; 435/69.1; 536/24.1; 514/44

(58) Field of Classification Search ................ 435/69.1, 435/173.3, 320.1, 252.3; 514/44; 536/24.1
See application file for complete search history.

(56) References Cited

U.S. PATENT DOCUMENTS 5,744,326 A * 4/1998 Ill et al. ..................... 435/69.1
5,981,274 A 11/1999 Tyrrell et al.

OTHER PUBLICATIONS

Anderson, W., *Human Gene Therapy*, Science, 256: 808–13 (1992).
Ausubel, F. et al. eds. *Current Protocols in Molecular Biology*, Wiley and Sons, New York, Suppl. 48 (1995).
Chaisomchit, S. et al., *Development of replicative and nonreplicative hepatitis B virus vectors*, Gene Therapy, 4: 1330–40 (1997).
Chiang P. et al., *Characterization of a cis Element Required for Packaging and Replication of the Human Hepatitis B Virus*, Virology, 186: 701–11 (1992).
Condreay, L. et al., *Replication of DHBV Genomes with Mutations at the Sites of Initiation of Minus–and Plus–Strand DNA Synthesis*, Virology, 188: 208–16 (1992).
Crystal, R., *Transfer of Genes to Humans: Early Lessons and Obstacles to Success*, Science, 270: 404–10 (1995).
Douglas, J. et al., *A system for the propagation of adenoviral vectors with genetically modified receptor specificities*, Nature Biotechnology, 17: 470–75 (1999).
Friedman T., *The Origins, Evolution, and Directions of Human Gene Therapy, The Development of Human Gene Therapy*, Cold Spring Harbor Laboratory Press, NY, (1999).

Galibert, F. et al., *Nucleotide sequence of the hepatitis B virus genome (subtype ayw) cloned in E. coli*, Nature, 28: 646–50 (1979).
Ganem, D. et al., *Hepadnaviridae and Their Replication*, Fundamental Virology, 3$^{rd}$ ed., 1199–1233 (1996).
Ganem, D. et al., *The Molecular Biology of The Hepatitis B Viruses*, Ann. Rev. Biochem., 56: 651–93 (1987).
Havert, M. et al., *cis–Acting Sequences in Addition to Donor and Acceptor Sites Are Required for Template Switching during Synthesis of Plus–Strand DNA for Duck Hepatitis B Virus*, Journal of Virology, 71: 5336–44 (1997).
Hirsh, R. et al., *cis–Acting Sequences Required for Encapsidation of Duck Hepatitis B Virus Pregenomic RNA*, Journal of Virology, 65: 3309–16 (1991).
Ho, T., et al., *Effects of Genomic Length on Translocation of Hepatitis B Virus Polymerase–Linked Oligomer*, Journal of Virology, 74: 9010–18 (2000).
Jeong, J. et al. *Evidence that the 5'–end Cap Structure Is Essential for Encapsidation of Hepatitis B Virus Pregenomic RNA*, Journal of Virology, 74: 5502–08 (2000).
Junker–Niepmann, M. et al., *A short cis–acting sequence is required for hepatitis B virus pregenome encapsidation and sufficient for packaging of foreign RNA*, The EMBO Journal, 9: 3389–96 (1990).
Loeb D. et al., *Mutations within DR2 Independently Reduced the Amount of both Minus– and Plus–Strand DNA Synthesized during Duck Hepatitis B Virus Replication*, Journal of Virology, 70: 8684–90 (1996).
Loeb D. et al., *Sequence Identity of the Terminal Redundancies on the Minus–Strand DNA Template Is Necessary but Not Sufficient for the Template Switch during Hepadnavirus Plus–Strand DNA Synthesis*, Journal of Virology, 71: 152–60(1997).
Loeb D. et al., *Sequence–independent RNA cleavages generate the primers for plus strand DNA synthesis is hepatitis B viruses: implications for other reverse transcribing elements*, The EMBO Journal, 10: 3533–540 (1991).
Loeb D. et al., *Transfer of the Minus Strand of DNA during Hepadnavirus Replication Is Not Invariable but Prefers a Specific Location*, Journal of Virology, 69: 6886–891 (1995).
Mulligan, R., *The Basic Science of Gene Therapy*, Science, 260: 926–32 (1993).

(Continued)

Primary Examiner—Laurie Scheiner
(74) Attorney, Agent, or Firm—Reed Smith LLP

(57) ABSTRACT

The present invention relates to novel hepatitis B virus vectors for use in gene therapy which can deliver therapeutic genes to liver cells. The invention also provides methods for the production of novel recombinant hepatitis B viruses. The recombinant viruses produced by this invention can deliver therapeutic genes specifically to liver cells either through in vivo or ex vivo therapy protocols. This vector can be used not only to treat liver diseases but also genetic diseases.

10 Claims, 11 Drawing Sheets

OTHER PUBLICATIONS

Nassal, M. et al., *A Bulged Region of the Hepatitis B Virus RNA Encapsidation Signal Contains the Replication Origin for Discontinuous First–Strand DNA Synthesis*, Journal of Virology, 70: 2764–73 (1996).

Nassal, M. et al., *Hepatitis B Virus Replication– an update*, Journal of Viral Hepatitis, 3: 217–26 (1996).

Nassal, M. et al., *Translational Inactivation of RNA Function: Discrimination against a Subset of Genomic Transcripts during HBV Nucleocapsid Assembly*, Cell, 63: 1357–63 (1990).

Pollack, J. et al., *Site Specific RNA Binding by a Hepatitis B Virus Reverse Transcriptase initiates Two Distinct Reactions: RNA Packaging and DNA Synthesis*, Journal of Virology, 68: 5579–87.

Protzer, U. et al., *Interferon gene transfer by a hepatitis B virus vector efficiently suppresses wild–type virus infection*, Proc. Natl. Acad. Sci., 96: 10818–23 (1999).

Sambrook et al., *Molecular Cloning: A Laboratory Manual*, Cold Spring Harbor Press $3^{rd}$ ed, (2001).

Seeger, C. et al., *Identification of a Signal Necessary for Initiation of Reverse Transcription of the Hepadnavirus Genome*, Journal of Virology, 65: 5190–95 (1991).

Sells, M. et al., *Replicative Intermediates of Hepatitis B Virus in HepG2 Cells That Produce Infectious Virions*, Journal of Virology, 62: 2836–44 (1988).

Shih, C. et al., In vitro *propagation of human hepatitis B virus in a rat hepatoma cell line*, Proc. Natl. Acad. Sci., 86: 6323–27 (1989).

Staprans, S. et al., *Mutations Affecting Hepadnvirus Plus–Strand DNA Synthesis Dissociate Primer Cleavage from Translocation and Reveal the Origin of Linear Viral DNA*, Journal of Virology, 65: 1255–62 (1991).

Wang, G, et al., *Novel Mechanism for Reverse Transcription in Hepatitis B Virus*, Journal of Virology, 67: 6507–12 (1993).

Wang, G. et al., *The Reverse Transcriptase of Hepatitis B Virus Acts As A Protein Primer for Viral DNA Synthesis*, Cell, 71: 663–70 (1992).

Yang, Y. et al., *Clearance of Adenovirus–Infected Hepatocytes by MHC Class I–Restricted $CD4^{+CTLs}$ In Vivo*, The Journal of Immunology, 155: 2564–70 (1995).

Yen, T., *Posttranscriptional Regulation of Gene Expression in Hepadnaviruses*, Virology, 8: 319–26 (1998).

\* cited by examiner

1. R711 (pCMV-HBV/GFP)

2. R712 (pCMV-HBV/GFP3.2)

Pre-S2/S promoter site

α, β cis-element

DR1, DR2

GFP(green fluorescence protein)

Transcription start site

HEPATITIS B VIRUS VECTORS FOR GENE THERAPY

FIELD OF THE INVENTION

The present invention relates to recombinant hepatitis B viral vectors useful for the expression of heterologous genes in liver cells. The invention also provides methods for the production of novel recombinant hepatitis B viruses. Liver-specific targeting ability of these HBV vectors extend its use for in vivo gene therapy protocol as well as for ex vivo therapy protocol. The recombinant viruses produced by this invention can deliver therapeutic genes specifically to liver cells either in vivo therapy protocol or ex vivo therapy protocol. This vector can be used not only to treat liver diseases but also genetic diseases.

BACKGROUND OF THE INVENTION

Gene therapy is considered as a new healer of modem medicine since genome sequencing is nearly completed (Anderson, 1992). Numerous methods for gene therapy have been developed in recent years (Mulligan, 1993). Gene therapy vectors used in current clinical trials can be divided into two groups: viral vectors such as retroviruses, adenoviruses or adeno-associated viruses (AAV) and nonviral vectors such as liposomes or naked DNAs (Friedmann, 1999). The most critical parameter of gene therapy is the efficiency of delivery of therapeutic genes to the recipient cells. To meet this goal, vectors need to not only specifically target recipient cells but also stably express therapeutic genes so that the therapeutic effect can be achieved. Lack of tissue-specificity and lack of long-term stable expression are serious drawbacks of current gene therapy vectors (Crystal, 1995).

To obtain efficient delivery of transgenes to target cells, viral vectors are frequently employed for gene therapy protocols. In particular, vectors that are used most often are those derived from retroviruses, adenoviruses or adeno-associated viruses (Crystal, 1995). These viral vectors are nonpathogenic and are designed to be replication-incompetent in recipient cells.

Most attempts to use viral vectors for gene therapy have relied on either retrovirus vectors or adenovirus vectors. Retroviral vectors are capable of maintaining stable gene expression because of their ability to integrate into the cellular genome. However, the disadvantages of retroviral vectors are becoming increasingly clear, including their tropism for dividing cells only, the possibility of insertional mutagenesis upon integration into the cell genome, decreased expression of the transgene over time and the possibility of generation of replication-competent retroviruses. On the other hand adenoviruses can infect nondividing cells, but can induce only transient expression of therapeutic genes. Further, repetitive administration of adenoviral vector to obtain long-term expression frequently induces severe inflammation (Yang et al., 1995). Evidently, these viral vectors need significant improvement before clinical use.

Although these viral vectors are most frequently used, they have a few unacceptable drawbacks. To improve the lack of tissue specificity, targeted viral vectors have been studied in laboratories (Douglas et al., 1999). However, it is not clear whether targeted viral vectors can be clinically used in the near future.

Regarding liver-directed gene therapy, the protocol for these viral vectors are by and large limited to ex vivo therapy, since these vectors lack tissue-specificity (i.e., hepatocyte-specificity). Ex vivo liver-directed therapy involves the surgical removal of liver cells, transduction of the liver cells in vitro (e.g., infection of the explanted cells with recombinant viral vectors) followed by injection of the genetically modified liver cells into the liver or spleen of the patient. A serious drawback for ex vivo liver-directed gene therapy is the fact that hepatocytes (i.e., liver cells) cannot be maintained and expanded in culture. Besides the technical difficulties and complexities, costs involved in each protocol are evidently astronomical.

Ideally, liver-directed gene therapy would be achieved by in vivo transfer of vectors which specifically target hepatocytes. Vectors derived from hepatotropic viruses, such as hepatitis B viruses (HBV), can be administered via circulation and target hepatocytes using the same receptor as the wild-type virus. However, the hepatitis B viruses have not been explored as a gene therapy vector due to lack of information on cis-acting elements essential for HBV genome replication.

Hepatitis B virus (HBV) is the prototype of the hepadnaviridae, a family of a small enveloped DNA virus with pronounced host and tissue specificity (Ganem, 1996). Hepadnaviruses have been found in mammals, e.g., human (HBV), woodchuck (WHV) and ground squirrels (GSHV), as well as in birds, e.g., Pekins ducks (DHBV) and grey herons (HHBV).

One of the bottlenecks in developing an HBV-derived gene therapy vector was a lack of information on cis-acting elements that are essential for viral genome replication. Thus, it is prerequisite to map cis-acting elements across the entire HBV genome.

SUMMARY OF THE INVENTION

The present invention comprises a novel hepatitis B virus vector and methods for making and using such vectors in liver-targeting gene therapy. The recombinant hepatitis B virus particles will specifically target hepatocytes of liver tissue. It is thought that the HBV vector will be particularly useful in gene transfer to liver tissue. Further, it is contemplated that the tissue specificity of the HBV vector will enable the HBV vector to be suitable even for in vivo therapy as well as ex vivo therapy. These novel HBV vectors may be used to deliver genes to liver in vivo by a variety of means including infection via circulation or direct injection of DNA into liver tissue.

The tropism of hepadnaviruses for hepatocytes has particular relevance to the use of HBV in gene therapy for diseases, which are caused by lack of gene expression in liver tissue. These diseases include numerous metabolic diseases, such as hemophilia lacking factor VIII or IV expression in liver. In addition, the HBV vector will be very useful to treat patients with chronic HBV infection. Since most hepatocytes of these chronic patients are equipped with packaging function (i.e., core, polymerase, and surface antigen expression), administration of the vector DNA could lead to packaging of the recombinant HBV particles, which could then infect neighboring hepatocytes. Thus, the vector DNA encoding various antiviral functions could induce therapeutic benefit. The vector DNA could be administered via direct intrahepatic injection or via circulation.

The invention provides information on two novel cis-acting elements of the hepatitis B virus genome that are essential for viral genome replication: α element and β element. The invention also provides a nucleotide sequence of the α element and β element.

The present invention is illustrated using recombinant HBV genome; however, the invention contemplates the use of other hepadnaviruses, including but not limited to woodchuck hepatitis virus (WHV), ground squirrel hepatitis virus (GSHV), and duck hepatitis B virus (DHBV). The art is well aware that the genomic organization of these hepadnaviruses is similar and that the teachings of the present invention can be translated to other hepadnaviruses.

In one embodiment of the present invention, the HBV vectors retain all cis-acting elements essential for viral genome replication. However, the present invention does not limit the position of the two novel cis-acting elements (i. e., α element and β element) at the indicated position on the map. In one embodiment, it is contemplated that in order to accomodate a larger insertion without exceeding the packaging size limit, the position of novel cis-acting elements could be changed without compromising vector function.

The present invention also delineates methods for the encapsidation of a recombinant hepatitis B virus genome, comprising the steps of providing: i) a recombinant HBV vector encoding at least one heterologous gene sequence inserted; ii) a helper plasmid capable of providing in trans hepatitis B virus gene products to complement the HBV vector for encapsidation and viral genome replication; and iii) introducing the recombinant HBV vector plasmid and a helper plasmid into the liver cell under conditions such that the recombinant HBV genome is encapsidated into the viral particles. It is contemplated that the liver cells of the present invention be selected from the group consisting of human liver cells including HepG2 cells, Huh7 cells, Chang liver cells, and rodent cells.

In one embodiment of the method, a heterologous gene sequences is inserted between the α element and DR2 of the prototype HBV vector (FIG. 10). In another embodiment of the method, it is contemplated that a heterologous gene sequences is inserted between 5' epsilon and the α element of the prototype HBV vector (FIG. 8).

A few attempts were made to generate recombinant HBV viruses, in which a subset of the HBV genome was substituted by heterologous genes (Chiang et al., 1992; Chaisomchit et al., 1997; Protzer et al., 1999). The present invention significantly differs from reported U.S. Pat. No. 5,981,274 as follows (Chaisomchit, et al., 1997). First of all, a heterologous sequence was inserted into the spacer (or tether) domain of the HBV polymerase ORF as a fusion protein in the patent above. Contrary to this, the present invention indicates that this insertion site overlaps with the α element found to be essential for the viral genome replication in this invention. Thus, the 50-fold reduction of the viral genome replication as indicated in the patent is a consequence of disruption of the α element in the vector. Further, the size of insert (267 bp or 374 bp) and its expression as a fusion protein limits its use as a vector. In conclusion, the recombinant HBV vector claimed in the patent above is defective or not capable of packaging a recombinant HBV genome encoding a heterologous gene sequence.

In addition, it has been claimed that two HBV mutants, in which a part of the HBV genome was substituted by the 0.7 K bp luciferase gene fragment, could produce virion particles in culture medium (Chiang et al., 1992). Further, the first successful production of recombinant hepadnaviruses (i. e., DHBV and HBV) encoding either GFP or interferon alpha were recently reported (Protzer et al., 1999). In both of these studies, without knowing the cis-elements essential for genome replication, they succeed in making recombinant hepadnaviruses when they substituted S ORF of DHBV or HBV with GFP or interferon-alpha in their recombinant vectors. The present invention significantly differs from the published reports in that this invention completely mapped cis-elements essential for viral genome replication. Based on the mapping data, this invention provides the prototype recombinant HBV vector in which heterologous sequences can be inserted into two different sites with an insert size of up to 0.90 K bp or 1.7 K bp, respectively.

Table 1. Summary of data obtained from a series of deletion mutants.

DETAILED DESCRIPTION OF THE INVENTION

A. Definitions

To facilitate understanding of the invention, a number of terms are defined below.

As used herein, the term "cis" is used in reference to the presence of genes on the same chromosome.

The term "trans-acting" is used in reference to the controlling effect of a regulatory gene on a gene present on a different chromosome.

As used herein, the term "in trans" is used in reference to indicate the complementation effect of a gene product on a gene present on a different chromosome.

The term "cis-acting" is used in reference to the controlling effect of a regulatory gene on a gene present on the same chromosome.

Nucleotide sequences of HBV genome were numbered according to Galibert et al. (Galibert et al., 1979), unless otherwise indicated. In this numbering system, the 5'-end of the pregenomic RNA is at nt. 1820 (Nassal et al., 1990). On the other hand, nucleotide sequences of the plasmids included in SEQ were numbered from the 5'-end of the pregenomic RNA.

B. Overview

1. Hepatitis B Viruses

Figure 1:
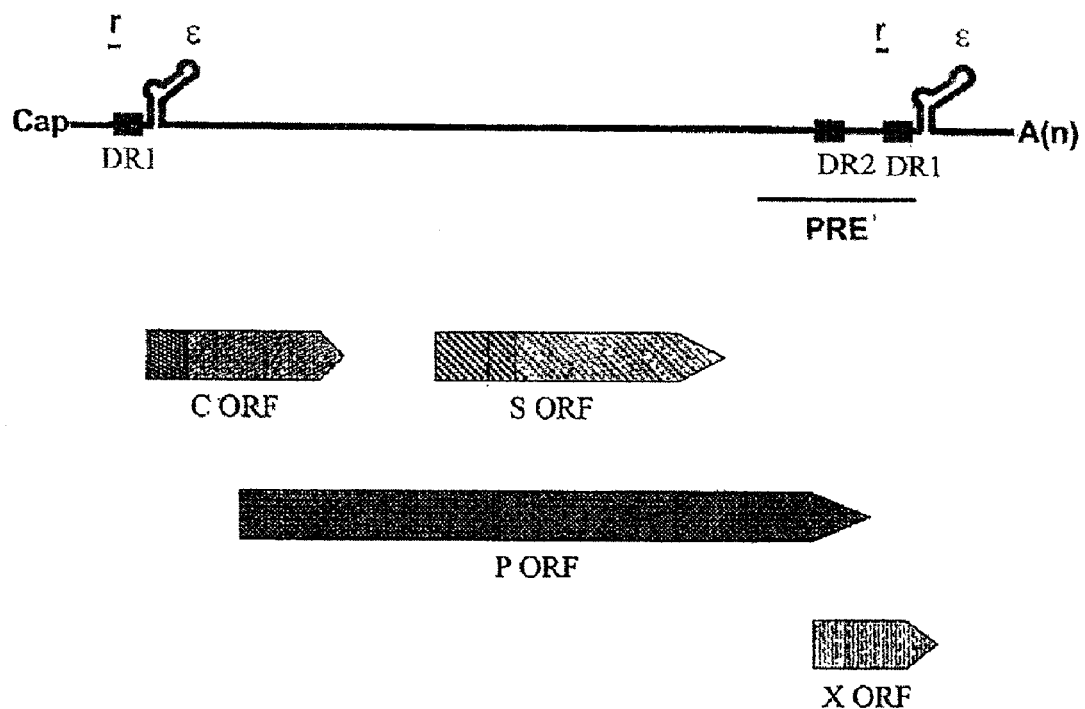
FIG. 1. A schematic representation of the pregenomic RNA of hepatitis B virus. cis-elements are indicated: DR1 (direct repeat 1), DR2 (direct repeat 2), epsilon (encapsidation signal), r (repeat) element, PRE (posttranscriptional RNA processing element). Four open reading frames of HBV are represented as arrowed open boxes: precore region (nt. 1816–1902), core region (nt. 1903–2454); pre-S1 region (nt. 2850–3173), pre-S2 region (nt. 3174–156), S region (nt. 157–837); P region (nt. 2310–1625), X region (nt. 1376–1840).

Hepatitis B virus (HBV), the causative agent of chronic hepatitis in man, is the prototype member of the hepadnaviridae (Ganem, 1996). Related members of the hepadnavirus family include woodchuck hepatitis virus (WHV), ground squirrel hepatitis virus (GSHV), and duck hepatitis B virus (DHBV). HBV genome is a circular DNA of only 3.2 K bp in length. The viral genome is a partially duplex circular DNA, possessing a single-stranded gap region in plus-strand DNA. Although HBV has a DNA genome, it replicates through reverse transcription of an RNA intermediate, the pregenomic RNA (pgRNA), within the subviral core particle. There are four major open reading frames (ORFs), all encoded in same strand (FIG. 1). Inspection of the sequence led to the recognition of conserved repeat elements that play important roles in the genome replication. These direct repeats (denoted DR1 and DR2) are located near the 5' end of the minus and plus DNA strands (FIG. 1).

Figure 2:
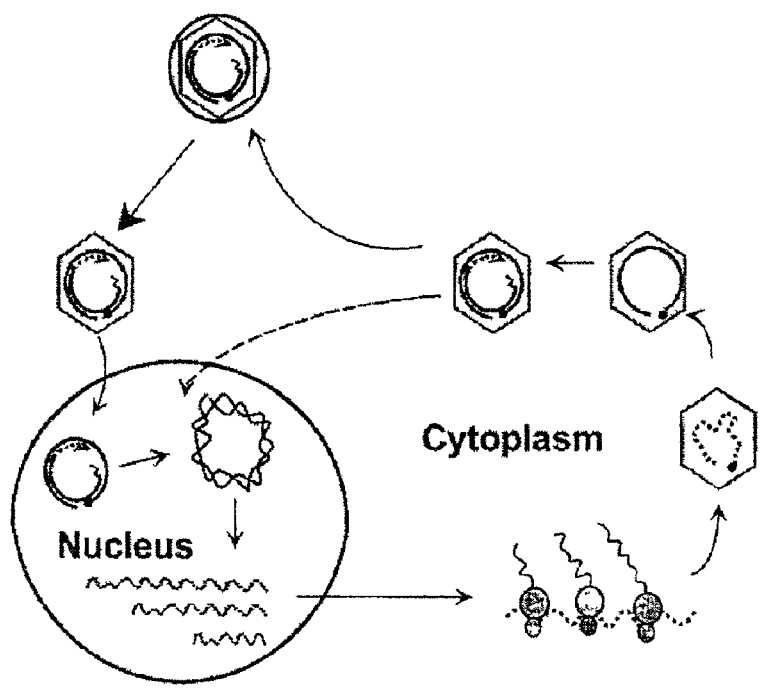
FIG. 2. Life cycle of hepadnaviruses.

The hepadnaviral life cycle is outlined in FIG. 2 (Ganem et al., 1987). Hepadnaviruses are thought to enter the hepatocytes through receptor-mediated endocytosis. Upon entry, a partial duplex genome is repaired to a covalently closed circular DNA (CCC), which is the template for transcription. Four viral transcripts are synthesized and transported to cytoplasm. The 3.5 K bp RNA, also called pregenomic RNA, serves as a template for reverse transcription as well as for translation of the core (C) and polymerase (P).

II. Reverse Transcription

Despite of the general similarities to retroviruses, many steps in its replication are distinct (Nassal et al., 1996). The first step of HBV genome replication is the encapsidation of the pregenomic RNA into core particles. Core particle assembly involves the interactions of the structural proteins, core (C) and polymerase (P) with the pregenomic RNA. Incorporation of P protein as well as the pregenomic RNA into assembling core particles is essential for viral DNA synthesis. The cis-acting element for encapsidation, termed ε, has been defined within 85 nucleotides (nt) near the 5' end of pgRNA, which is necessary and sufficient to direct encapsidation of heterologous RNA sequences into viral core particle (Junker-Niepmann et al., 1990; Hirsch et al., 1991). The epsilon element can fold into a stem-loop structure, which is highly conserved among hepadnaviruses.

Figure 3:
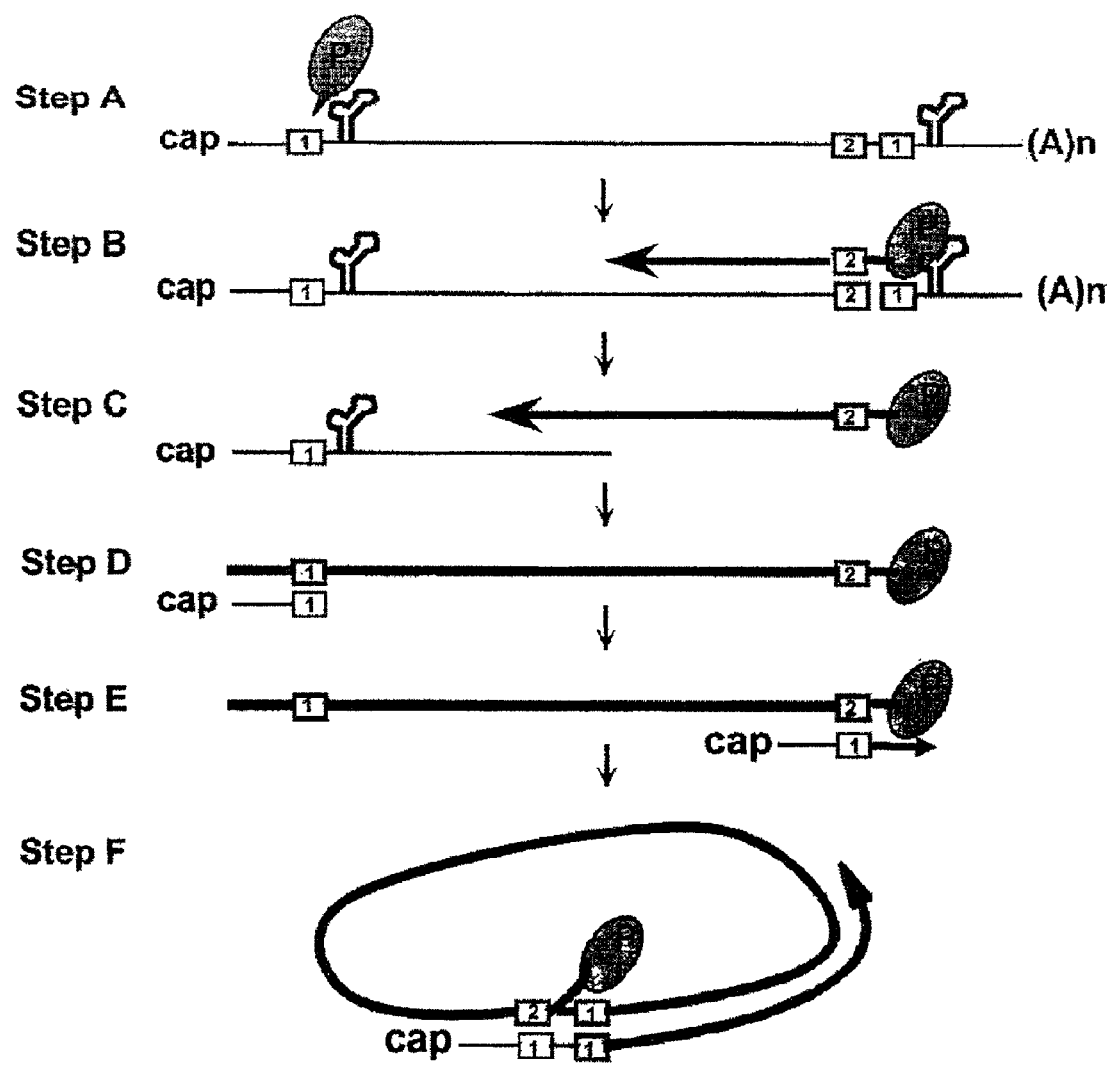
FIG. 3. Model for the synthesis of hepadnaviral DNA through reverse transcription of the pregenomic RNA as a template for the viral polymerase. (see text for explanation).

Reverse transcription mechanism of HBV polymerase is quite complicated, as expected from its peculiar genome structure. A process described as template switching is required for the successful synthesis of a double-stranded DNA product (FIG. 3). First, minus-strand DNA synthesis is initiated near the 5'-end of its template, the pregenomic RNA (Loeb et al., 1995). The viral polymerase is both the primer and polymerase for minus-strand DNA synthesis (Wang et al., 1992). Following template switching to an acceptor site near the 3' end of the pregenomic RNA, minus-strand DNA synthesis resumes at this position, resulting in a genome-length, minus-strand DNA. Upon completion of the synthesis of minus-strand DNA, the final RNase H cleavage product, the 18-nt RNA fragment, serves as a primer for the initiation of plus-strand DNA synthesis (Loeb et al., 1991). Upon translocation to DR2, the RNA primer is used for the initiation of plus-strand DNA synthesis. For the plus-strand DNA initiated at DR2, a third template switch, termed circularization, is required to generate a mature relaxed circular DNA.

IV. Cis-acting Elements Essential for HBV Genome Replication

Molecular analysis revealed that several elements play a role in the viral DNA synthesis (Nassal et al., 1996). The list of cis-acting elements includes: 5' epsilon, encapsidation signal (Junker-Niepmann et al., 1990; Hirsch et al., 1991); DR1 and DR2, primer acceptor sites for primer translocation step during viral DNA synthesis (Nassal et al., 1996); r (repeat) for circularization (Loeb et al., 1997); and PRE, posttranscriptional RNA processing element (Huang et al., 1995). All of these known elements are located to either side of the HBV pregenome (FIG. 1). In the case of DHBV, three additional elements, termed 3E, M and 5E, have been reported to be essential for template switching during plus-strand DNA synthesis (Havert et al., 1997). However, it is not known whether any other elements in the middle of the viral genome are essential for HBV genome replication. HBV genome has not been explored as a gene therapy vector, primarily due to the lack of information on its cis-acting elements.

V. Design of the Prototype HBV Vector

Figure 4:
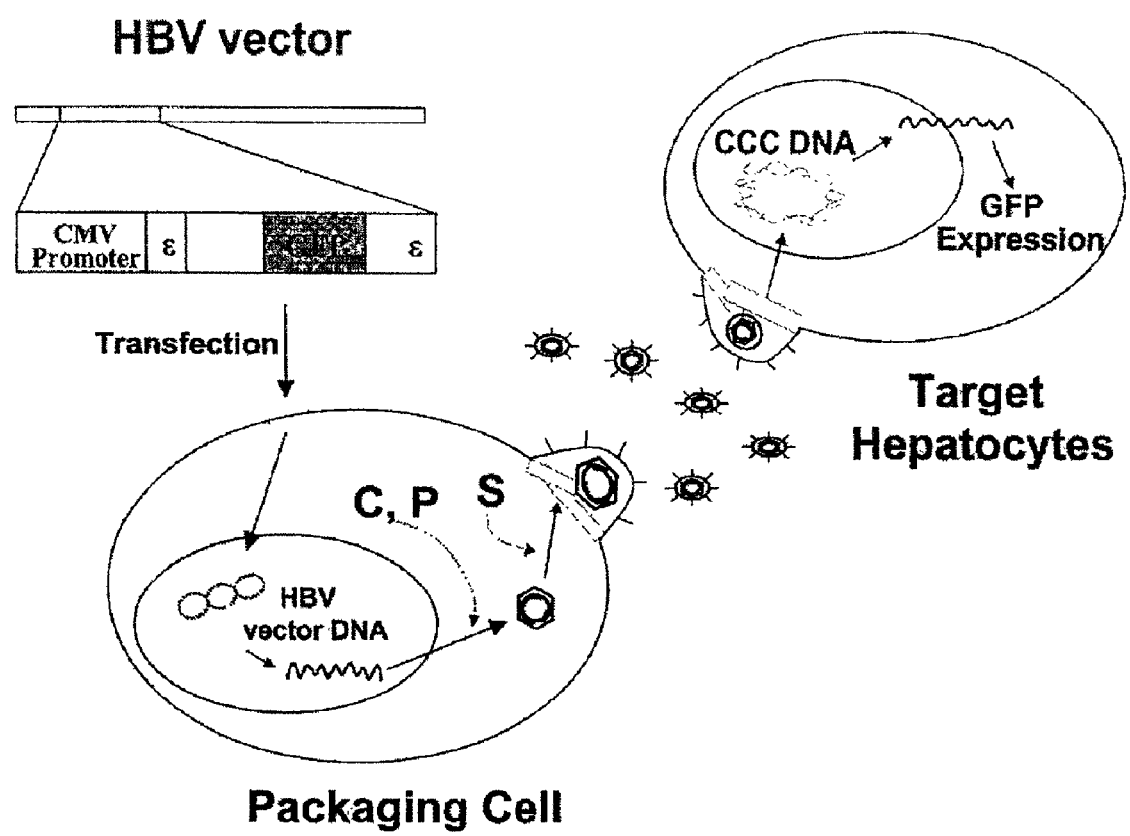
FIG. 4. A schematic representation of gene therapy procedure using the hepatitis B virus vector to deliver a heterologous gene (e. g., GFP) to liver cells. A recombinant HBV vector DNA encoding GFP gene is transfected into a packaging cell line that expresses viral proteins necessary for packaging the recombinant HBV genome. The produced recombinant HBV particles then infect hepatocyctes. Upon the entry of the HBV particles into cells, the viral DNA is repaired to CCC (covalently closed circular) form DNA in the nucleus and induces the expression of GFP, as the wild-type HBV does. The packaging cell line can be replaced by a helper plasmid that provides core and the viral polymerase.
Figure 5A:
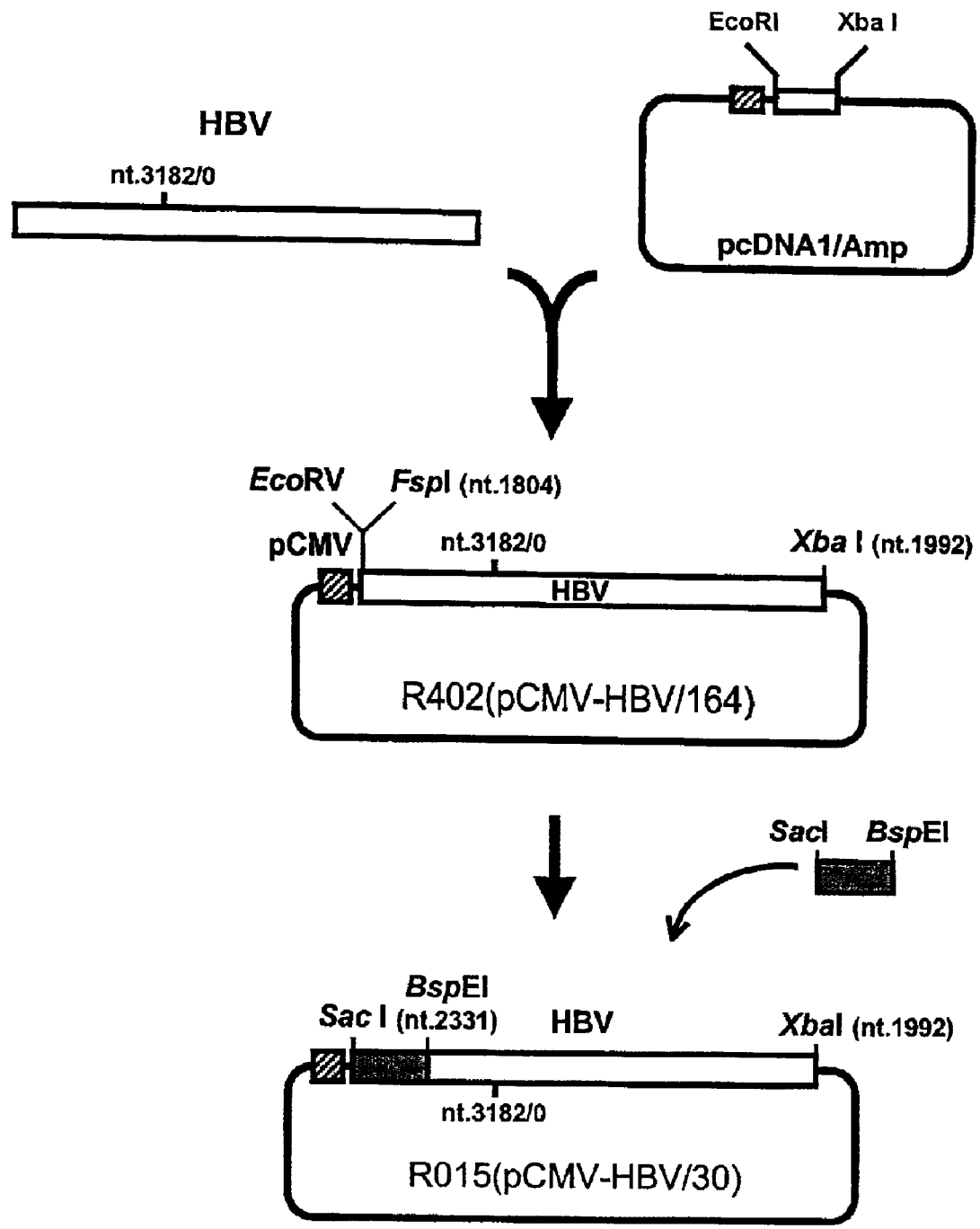
FIG. 5a. A schematic representation of the subcloning procedure of R015 plasmid.
Figure 5B:
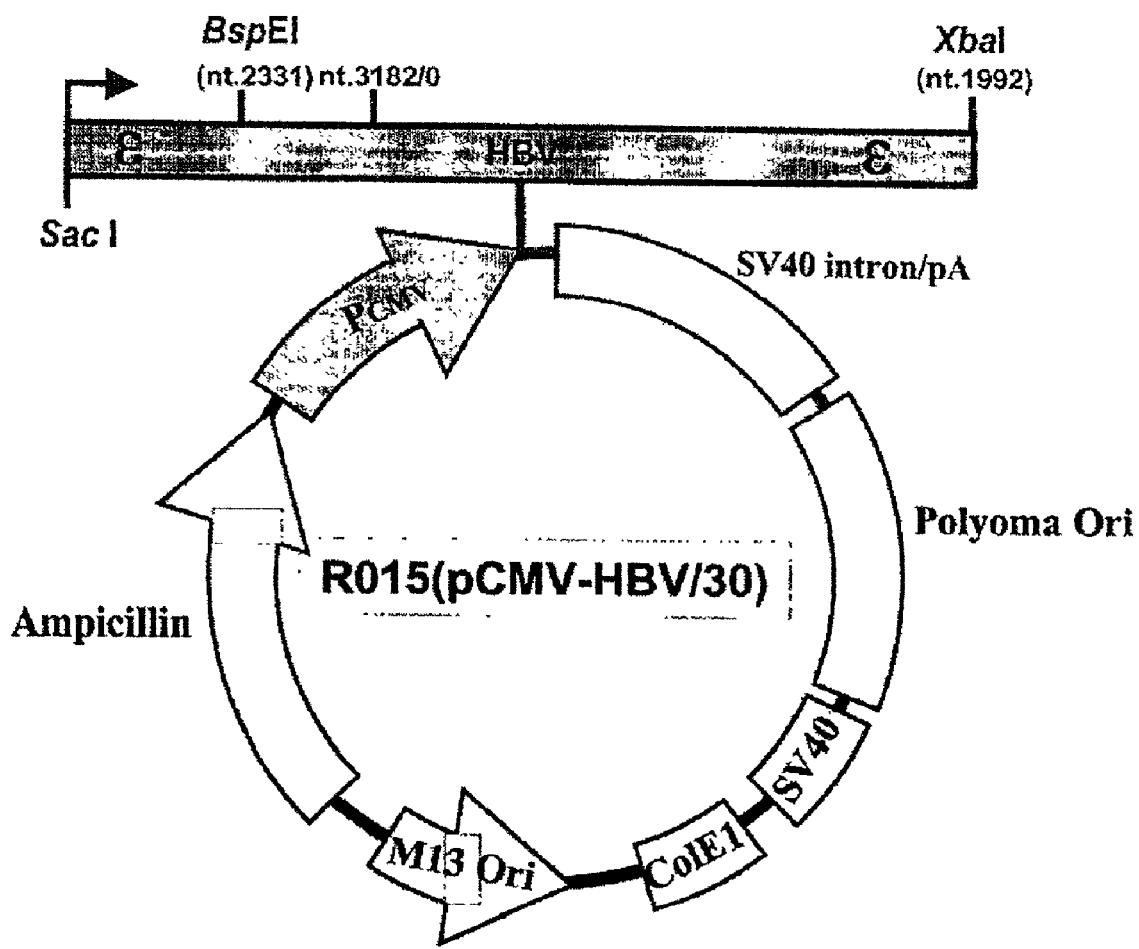
FIG. 5b. Map of R015 plasmid. Nucleotide sequence of R015 plasmid is attached in SEQ ID 3.

Having identified all cis-acting elements required for HBV genome replication, it is possible to design a gene therapy vector that can accomodate a heterologous gene sequence without compromising its ability to replicate, if trans-acting factors are provided in trans. Briefly, the HBV vector encodes all cis-acting elements that are essential for the viral genome replication, but lacks expression of the viral proteins. Nonetheless, the recombinant virus can be produced if the viral proteins (i. e., core, polymerase, surface antigens) are provided in trans via a helper plasmid or packaging cell lines (FIG. 4).

Figure 8:
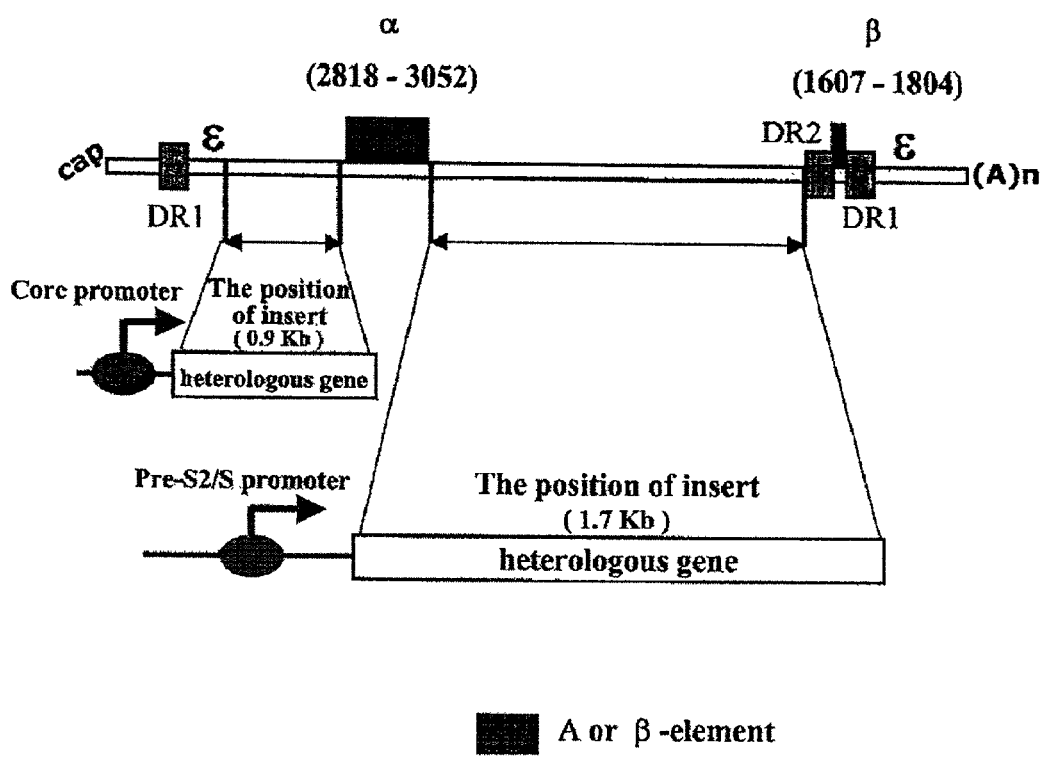
FIG. 8. Map of the prototype HBV gene therapy vector. Sequence elements of the HBV vector are drawn on the pregenomic RNA. Two novel cis-elements; α element, βelement. Two proposed insertion sites are indicated by open boxes. Appropriately located viral promoters are indicated; core promoter and pre-S2/S promoter, respectively.

Several issues need to be considered for the design of a gene therapy vector including insertion site, size of insert(s), promoter to drive transgene transcription. First of all, two insertion sites were selected; one between 5' epsilon and the α element, the other site located between the α element and DR2 (FIG. 8). These two insertion sites were selected since these sequences are dispensable for viral genome replication. Regarding insert size, fragments of up to 0.90 K bp and 1.7 K bp, respectively, can be inserted into these two insertion sites without significantly exceeding the wild-type genome size. Two endogenous viral promoters (i. e., core promoter and pre-S2/S promoter), conveniently located just upstream of these two insertion sites, are employed to drive transcription. Further, this HBV vector can be used as a bicistronic expression vector, if two insertion sites are used simultaneously (FIG. 8).

C. Experimental

Most of the techniques used for vector construction and cell transfection are widely practiced in the art, and most practitioners are familiar with standard resource materials describing specific conditions and procedures.

Construction of the vectors of the invention employs standard ligation and restriction techniques which are well understood in the art (see Sambrook et al., 2001).

In this experimental disclosure, the following abbreviations are applied: M (molar), mM (millimolar), ml (milliliters), μg (micrograms), mg (milligrams), PEG (polyethylene glycol), ORF (open reading frame), The following examples are presented to illustrate the present invention and to assist one of ordinary skill in making and using the same. The examples are not intended in any way to otherwise limit the scope of the disclosure.

EXAMPLE 1

Construction of a Replication-competent Plasmid for Wild-type HBV

To design a HBV gene therapy vector, it is prerequisite to map all the cis-acting elements that are essential for the viral genome replication. To achieve this, a replication-competent plasmid that can lead to the production of infectious HBV particles upon transfection was constructed. The fact that a heterologous promoter driven RNA transcript analogous to the pregenomic RNA can lead to the production of infectious viral particles are well understood in the art (Nassal et al., 1990). Thus, a pregenomic RNA expression plasmid was designed such that the 5'-end of the transcripts would be identical to that of wild-type HBV. Specifically, the position of 5'-epsilon element is 30 nucleotides away from the 5'-end (Jeong et al., 2000).

The nucleotide sequence of the HBV genome was numbered starting at the unique Eco RI site of HBV ayw subtype, according to the method of Galibert et al. (Galibert et al., 1979). Nucleotide numbers (nt.) indicate the HBV sequence number, unless otherwise indicated. In this number system, the 5' end of the pregenomic RNA is at nt. 1820 (Nassal et al., 1990).

1-1. Construction of R402 Plasmid (pCMV-HBV/164):

To generate a replication-competent HBV construct, the greater-than-genome-length viral genome should be inserted downstream of the promoter element to maintain terminal redundancy of the pregenomic RNA (see FIG. 1; Ganem et al., 1987). The genome of hepatitis B virus was derived from pSV2A-Neo(HBV)2 plasmid that contains a dimer of HBV ayw subtype (Shih et al., 1989). The greater-than-genome-length Fsp I(nt. 1804)-to-Xba I(nt. 1992) fragment (3354 nt) of HBV ayw subtype (Galibert et al., 1979) was inserted into Eco RV and Xba I sites in the multiple cloning site of pcDNA1/Amp plasmid (Invitrogen, U.S.A.): R402 plasmid (pCMV-HBV/164). The HBV transcript made from this plasmid (pCMV-HBV/164) has a vector-derived 134 nt at the 5' end relative to that of wild-type pregenomic RNA.

1-2. Construction of R015 Plasmid (pCMV-HBV/30):

To make a RNA expression plasmid that can transcribe the HBV pregenomic RNA that is almost identical to the wild-type pregenomic RNA with respect to the position of the epsilon element, a small deletion was introduced into R402 plasmid (pCMV-HBV/164). Thus, R015 plasmid (pCMV-HBV/30) was made by removing this pcDNA1/Amp plasmid-derived 134 nucleotides by a PCR-mediated method (Jeong et al., 2000).

Briefly, a fragment was made by polymerase chain reaction using a forward primer of the sequence 5-CCC GAGCTCTCTGGCTAACTAACTTTTTCACCTCTGCC-3 (SacI site underlined) and a reverse primer of the sequence 5-CCCAAGCTTCTATTGTTCCCAAGAATATGG-3 (nt 2839 to 2822) with R402 (pCMV-HBV/164) as a template. The resulting PCR fragment was digested by SacI and BspEI and then inserted between the SacI (nt. 2894 of pcDNA1/amp) and BspEI (nt. 2331) site of R402 (pCMV-HBV/164).

1-3. Construction of R063 (pCMV-CPS) Helper Plasmid

Briefly, PCR was carried out using a forward primer with EcoR I site and a reverse primer with Xho I site to generate the EcoR I-to-Xho I fragment (nt. 1903-to-2454) Then, the 0.5 K bp PCR product was inserted into pcDNA3 (Invitrogen, U.S.A) via EcoR I, Xho I restriction sites to make R062 plasmid. Next, the BspE I (nt. 233 1)-to-Apa I of R062 plasmid was substituted by 2.6 K bp BspE I (nt. 2331)-to-Apa I of R015 plasmid. This R063 plasmid lacking encapsidation signal, epsilon, was employed as helper plasmid to provide the viral proteins (i. e., core, polymerase, surface antigen) essential for the viral replication and assembly.

Forward primer: 5'-CATG GAATTCATGGACATCGACCCT-3

(EcoR I site underlined)

Reverse primer: 5'-CCG CTCGAGCTAACATTGAGATTCCCGAGA-3'

(Xho I site underlined)

Forward primer: 5'-CATG GAATTCATGGACATCGACCCT-3

(EcoR I site underlined)

Reverse primer: 5'-CCG CTCGAGCTAACATTGAGATTCCCGAGA-3'

(Xho I site underlined)

EXAMPLE 2

Demonstration of replication-competency of wild-type pregenomic RNA expression plasmid, R015 plasmid (pCMV-HBV/30).

2-1. Cell Growth, Transfection of Heptoma Cell Lines

Human hepatoma cells, designated Huh7 cells were grown in DMEM (Gibco-BRL) supplemented with 10% fetal bovine serum (Gibco-BRL) and 10 □ of gentamicin per mL and were split every third day. The day before transfection, cells were plated at a confluency of 75%. On the following day, cells were washed twice with phosphate-buffered saline (PBS) and given fresh media. After 2 hours, cells were transfected with 10 □ of supercoiled plasmid DNA per 60 mm plate by the CaPO4 coprecipitation technique.

2-2. Southern Blot Analysis of the Viral Replication-intermediate from Cytoplasmic Core Particles.

Three days after transfection, viral DNAs were extracted from intracellular core particles by PEG precipitation as described previously (Staprans et al., 1991). Briefly, transfected cells from a 100-mm plate were lysed in lysis buffer [10 mM Tris (pH 7.5), 1 mM EDTA, 50 mM NaCl, 8% sucrose, 0.25% Nonidet P-40]. Nuclei were removed by centrifugation for 3 min in a microcentrifuge, and the cytoplasmic extract was adjusted to 6 mM $MgCl_2$ and digested with DNase I (50 □/□) for 30 min at 37° C. Cores were precipitated by centrifugation for 4 min after adding 4×PNE buffer [26% PEG, 1.4 M NaCl, 25 mM EDTA], and incubating at 4° C. for 30 min. Core particles resuspended in buffer [10 mM Tris (pH 7.5), 6 mM $MgCl_2$] were then digested with DNase I for an additional 15 min at 37° C., followed by the addition of 5 mM EDTA, 1% SDS, and 500 □ of proteinase K per □ and were incubated for 1 h at 37° C. Core nucleic acid was extracted twice with phenol/$CHCl_3$ (1:1) and precipitated with ethanol, then resuspended in 50 □ of TE [10 mM Tris(pH 7.5), 1 mM EDTA].

Extracted viral DNA were subjected to agarose gel electrophoresis, followed by Southern blot analysis, which are well known to those skilled in the art (*Current Protocols in Molecular Biology*, Ausubel, F. et al., eds., Wiley and Sons, New York, 1995).

EXAMPLE 3

Deletion mutants of R015 plasmid (pCMV-HBV/30).

A series of small deletion mutants were generated by standard recombinant DNA technology (Sambrook et al., 2001).

3-1. R060(pCMV-ayw Δ1910–1992) Plasmid

Plasmid R059(pBS+Δ1910–1992) was made in which the Sac I-to-EcoR I(nt. 3182) fragment of HBV ayw subtype, but lacking the nt. 1910–1992 fragment (Galibert et al., 1979) was subcloned into pBluescript SK(+) plasmid (Stratagene, USA). Subsequently, the Sac I-to-EcoR I fragment of R015 was replaced by the Sac I-to-EcoR I fragment of R059 to generate R060 plasmid.

3-2. R048(pCMV-ayw Δ1884–2459) Plasmid

First, plasmid R046 was made in which the Sac I-to-EcoR I(nt. 3182) fragment of HBV ayw subtype (Galibert et al., 1979) was subcloned into pCH110 (Pharmacia). Then, R047 plasmid was generated by deleting the 151 bp Xba I fragment (nt. 1992–2143). Subsequently, the Sac I-to-EcoR I fragment of R015 plasmid was replaced by the Sac I-to-EcoR I fragment of R047 to generate R048 plasmid.

3-3. R056(pCMV-ayw Δ2143–2459) Plasmid

First, plasmid R049 was made in which the Sac I-to-EcoR I(nt. 3182) fragment of HBV ayw subtype (Galibert et al., 1979) was subcloned into pBluescript II KS(+) (Stratagene, U.S.A.). The Sty I(nt. 1884)-to-Sty I(nt. 2459) fragment of R049 was replaced by a PCR product of Sty I(nt. 1884)-to-Xba I(nt. 2143) fragment encoding Sty I restriction site at the 5'-end of the reverse primer to make R051 plasmid. Subsequently, the Sac I-to-EcoR I fragment of R015 was replaced by the Sac I-to-EcoR I fragment of R051 plasmid to generate the R056 deletion mutant.

Forward primer: 5-CCCGAGCTCTCTGGCTAACTAACTTTTCACCTCTGCC-3 (Sac I site underlined)

Reverse primer: 5'-CCCCCCAAGGCGCTGGATCTTCCAAATT-3' (Sty I site underlined)

3-4. R021(pCMV-ayw Δ2459–2817) Plasmid

First, plasmid R407 was made in which the Sac I-to-Xho I(nt. 129) fragment of R015 plasmid was subcloned into pBlueBacHis2 plasmid (Invitrogen, U.S.A.). Then, the Sty I(nt. 2459)-to-BstE II(nt. 2817) fragment of R407 was deleted and filled in by Klenow fragment to make R018 plasmid. Subsequently, the BspE I (nt. 2331)-to-EcoR I (nt. 3182) fragment of R015 was replaced by the BspE I-to-EcoR I fragment of R018 to generate R021 deletion mutant.

3-5. R022(pCMV-ayw Δ2662–3182) Plasmid

To make R022, the BstE II(nt. 2662)-to-EcoR I(nt. 3182) fragment of R015 plasmid was deleted and filled in by Klenow fragment to make R022 plasmid.

3-6. R045(pCMV-ayw Δ2839–3182) Plasmid

First, plasmid R701 was made in which the BstE II(nt. 2817)-to-Sph I(nt. 1239) fragment of R015 plasmid was subcloned into pGEM-4Z plasmid (Promega, U.S.A). Then, the Bgl II(nt. 2839)-to-EcoR I(nt. 3182) fragment of R701 was deleted and filled in by Klenow fragment to make R043 plasmid. Subsequently, the BstX I (nt. 2817)-to-BstX I(nt. 620) fragment of R015 was replaced by the corresponding 642 bp BstX I fragment of R043 to generate R045 deletion mutant.

3-7. R044(pCMV-ayw Δ3052–3182) Plasmid

The Bsu36 I(nt. 3052)-to-EcoR I(nt. 3182) fragment of R701 was deleted and filled in by Klenow fragment to make R042 plasmid. Subsequently, the BstX I (nt. 2817)-to-BstX I(nt. 620) fragment of R015 was replaced by the corresponding 855 bp BstX I fragment of R042 plasmid to generate R044 deletion mutant.

3-8. R023(pCMV-ayw Δ3182–129) Plasmid

To make R023, the EcoR I(nt. 3182)-to-Xho I(nt. 129) fragment of R015 was deleted and filled in by Klenow fragment to make R023 plasmid.

3-9. R040(pCMV-ayw Δ129–490) Plasmid

First, plasmid R037 was made in which the EcoR I(nt. 3182)-to-Sph I(nt. 1239) fragment of R015 plasmid was subcloned into pGEM-4Z plasmid (Promega, U.S.A). The Xho I(nt. 129)-to-BamH I(nt. 490) fragment of R037 plasmid was deleted and filled in by Klenow fragment to make R038 plasmid. Subsequently, the EcoR I (nt. 3182)-to-Sph I(nt. 1238) fragment of R015 plasmid was replaced by the corresponding 877 bp EcoR I-to-Sph I fragment of R038 plasmid to generate R040 deletion mutant.

3-10. R041(pCMV-ayw Δ490–827) Plasmid

The BamH I(nt. 490)-to-Acc I(nt. 827) fragment of R037 was deleted and filled in by Klenow fragment to make R039 plasmid. Subsequently, the EcoR I (nt. 3182)-to-Sph I(nt. 1238) fragment of R015 plasmid was replaced by the corresponding 897 bp EcoR I-to-Sph I fragment of R039 to generate R041 deletion mutant.

3-11. R025(pCMV-ayw Δ827–1238) Plasmid

First, a plasmid R050 was made in which the EcoR I(nt. 3182)-to-Apa I fragment of R015 plasmid was subcloned into pBluescript II KS(+) (Stratagene, U.S.A.). The Acc I(nt. 827)-to-Sph I(nt. 1238) fragment of R050 plasmid was deleted and filled in by T4 DNA polymerase to make R008 plasmid. Subsequently, the EcoR I (nt. 3182)-to-Apa I fragment of R015 was replaced by the corresponding 1591 bp EcoR I-to-Apa I fragment of R008 to generate R025 deletion mutant.

3-12. R026(pCMV-ayw Δ1238–1374) Plasmid

The Sph I(nt. 1238)-to-Nco I(nt. 1374) fragment of R050 was deleted and filled in by T4 DNA polymerase to make R009 plasmid. Subsequently, the EcoR I (nt. 3182)-to-Apa I fragment of R015 plasmid was replaced by the corresponding 1866 bp EcoR I-to-Apa I fragment of R009 plasmid to generate R026 deletion mutant.

3-13. R027(pCMV-ayw Δ1374–1419) Plasmid

The Nco I(nt. 1374)-to-Aat II(nt. 1419) fragment of R050 plasmid was deleted and filled in by T4 DNA polymerase to make R012 plasmid. Subsequently, the EcoR I (nt. 3182)-to-Apa I fragment of R015 was replaced by the corresponding 1957 bp EcoR I-to-Apa I fragment of R012 to generate R027 deletion mutant.

3-14. R028(pCMV-ayw Δ1419–1804) Plasmid

The Aat II(nt. 1419)-to-Fsp I(nt. 1804) fragment of R050 was deleted and filled in by T4 DNA polymerase to make R013 plasmid. Subsequently, the EcoR I (nt. 3182)-to-Apa I fragment of R015 was replaced by the corresponding 1617 bp EcoR I-to-Apa I fragment of R013 to generate R028 deletion mutant.

3-15. R053(pCMV-ayw Δ1419–1592) Plasmid

The Aat II(nt. 1419)-to-Apa I fragment of R050 was replaced by the PCR product of Aat II(nt. 1592)-to-Apa I fragment encoding Aat II restriction site at the 5'-end of the forward primer to make R052 plasmid. Subsequently, the EcoR I-to-Apa I fragment of R015 was replaced by the EcoR I-to-Apa I fragment of R052 to generate R053 deletion mutant.

3-16. R035(pCMV-ayw Δ1607–1804) Plasmid

The EcoR I(nt. 3182)-to-Bsa I(nt. 1607) blunted fragment of R050 plasmid was ligated with the EcoR I(nt. 3182)-to-Fsp I(nt. 1804) of R015 plasmid to make R035 plasmid.

3-17. R029(pCMV-ayw Δ1804–1884) Plasmid

The Fsp I(nt. 1804)-to-Sty I(nt. 1884) fragment of R050 was deleted and filled in by Klenow polymerase to make R010 plasmid. Subsequently, the EcoR I (nt. 3182)-to-Apa I fragment of R015 was replaced by the corresponding 1922 bp EcoR I-to-Apa I fragment of R010 to generate R029 deletion mutant.

EXAMPLE 4

Figure 11A:
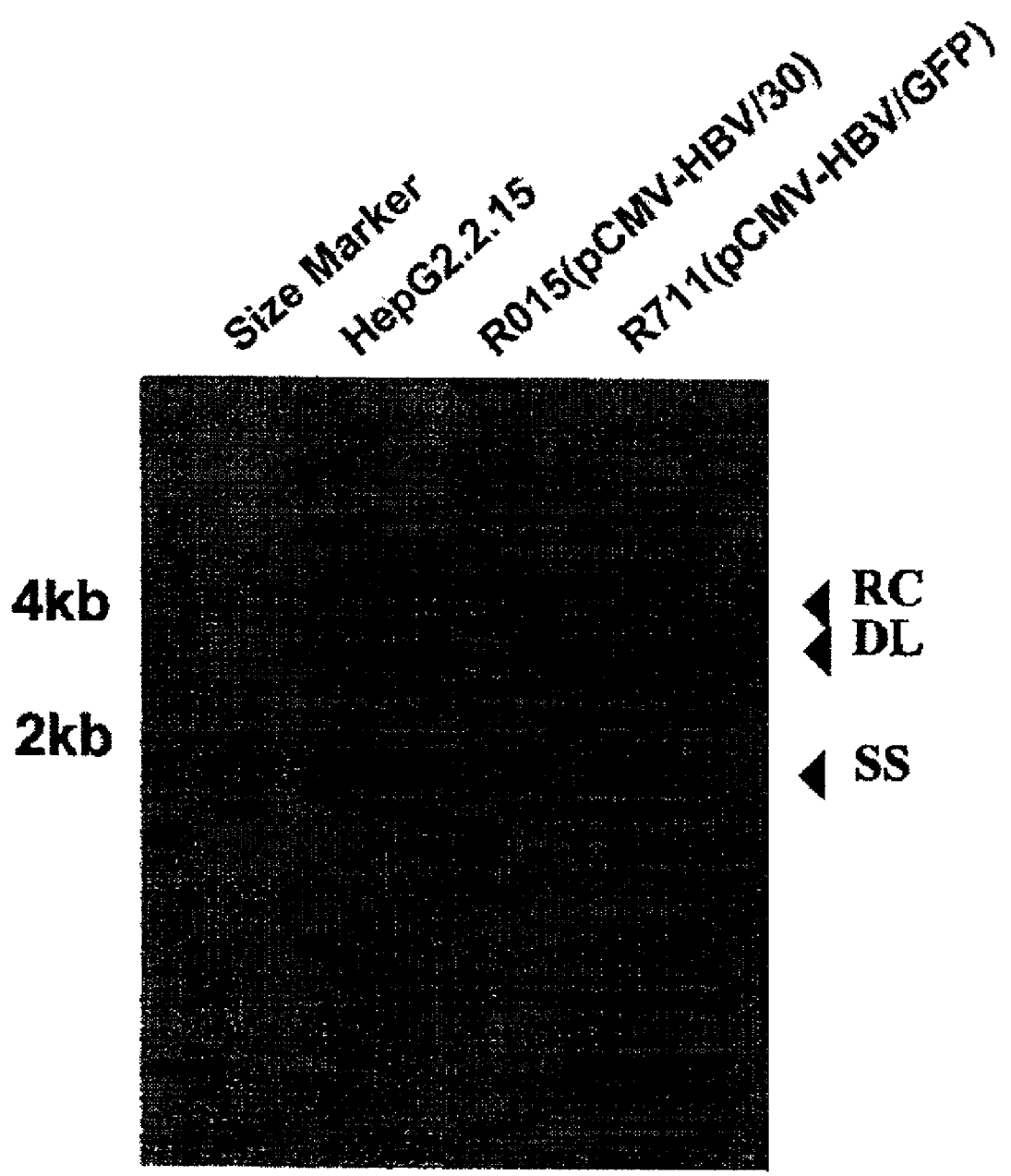
FIG. 11a. An autoradiograph of Southern blot analysis of R711 plasmid. HBV probe was used to detect the viral replication-intermedaites. RC, relaxed circular DNA; DL, double-stranded linear DNA; SS, single-stranded DNA.
Figure 11B:
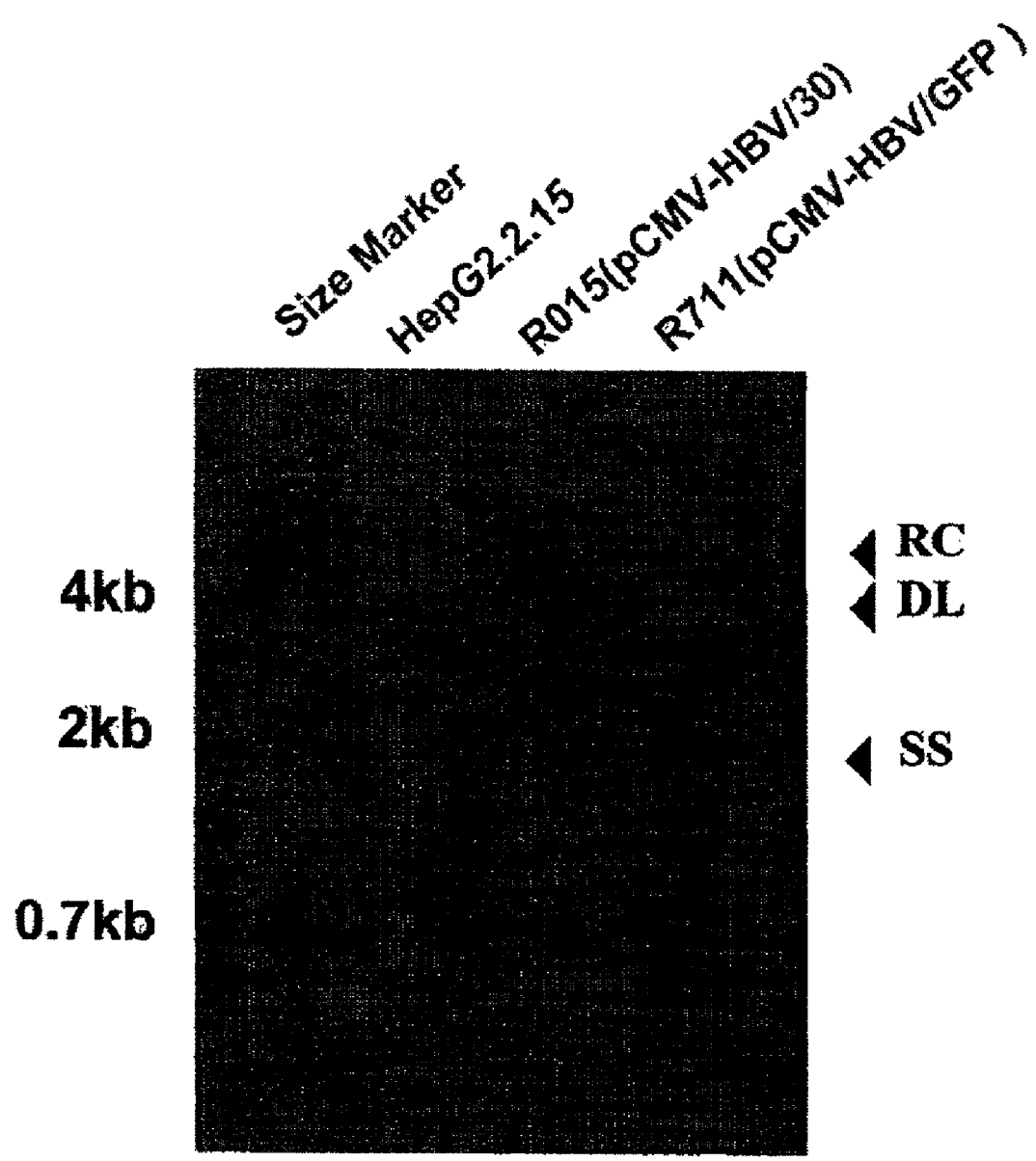
FIG. 11b. An autoradiograph of Southern blot analysis of R711 plasmid. GFP probe was used to detect the viral replication-intermediates. RC, relaxed circular DNA; DL, double-stranded linear DNA; SS, single-stranded DNA.

Analysis of cis-elements Essential for HBV Genome Replication 4-1. Extraction of Core-associated DNA and Southern Blot Analysis Transfection, DNA extraction and Southern blots were performed as described in EXAMPLE 2-2. To complement trans-acting viral proteins, a helper plasmid (pCMV-CPS) that provides core protein and polymerase was cotransfected along with each deletion mutant during transfection. FIG. 11 showed a typical Southern blot result. As described above, three species of the HBV replication-intermediates can be seen in this Southern blot of core-associated viral DNA: SS (single-stranded DNA), DL (double-stranded linear DNA), and RC (relaxed circular DNA). RC form is the mature product of viral genome replication found in virions. Thus, lack of the RC form DNA in Southern blots would indicate that a cis-acting element essential for the viral genome synthesis is deleted in the mutants.

4-2. Analysis of cis-elements Essential for HBV Genome Replication.

A series of deletion mutants was generated that encompass the entire HBV genome. Each deletion lacks a fragment of between 0.05–0.52 K bp. Southern analysis indicated that only SS DNA was detected from cells transfected by the R022 mutant (pCMV-ayw Δ2662–3182/0). To delineate the region deleted in mutant R022, two addition mutants were made: R045 (pCMV-ayw Δ2839–3182/0) and R044 (pCMV-ayw Δ3052–3182/0). As a result, RC DNA as well as SS DNA and DL DNA were detected in cells transfected by R044 mutants. Thus, a sequence deleted in the R044 mutant is not essential for viral genome synthesis. On the other hand, only trace amount of SS DNA was detected in Southern blots of cells transfected by mutant R045. Thus, a sequence deleted in R045 is essential for the viral genome replication. Taken together, a novel cis-element essential for HBV genome replication, termed α element (nt 2662–3052), was identified.

In addition, mutant R028 (pCMV-ayw Δ1419–1804) lacking the DR2 element (nt. 1592–1602) was made. Southern blot analysis of cells transfected by R028 (pCMV-ayw Δ1419–1804) showed the detection of only SS DNA, but not RC DNA. This result is consistent with published reports on the role of DR2 on minus-strand DNA synthesis in DHBV (Loeb et al., 1996; Condreay et al., 1992). To delineate this region further, mutant R053 (pCMV-ayw Δ1419–1592) lacking sequence upstream of DR2 element was made. Southern blot analysis indicated detection of RC DNA from cells transfected by mutant R053. This result indicated that the sequence lacking in the R053 mutant is dispensable for HBV genome replication. To further delineate this region, R035 mutant (pCMV-ayw Δ1607–1804) lacking a sequence between DR2 and DR1 elements was made. Even SS DNA was not detected from cells transfected by the R035 mutant. Thus, the sequence between DR2 and DR1 element, termed β element, is essential for the minus-strand DNA synthesis. In addition, R029 mutant (pCMV-ayw Δ1804–1884) lacking DR1 element was made. Consistent with published data, no SS DNA was detected (Condreay et al., 1992).

In contrast, sequences deleted in some of the deletion mutants turned out to be dispensable. These mutants included R060 mutant (pCMV-ayw Δ1910–1992), R048 mutant (pCMV-ayw Δ1992–2143), R056 mutant (pCMV-ayw Δ2143–2459), R021 mutant (pCMV-ayw Δ2459–2817), R044 mutant (pCMV-ayw Δ3052–3182), R023 mutant (pCMV-ayw Δ3182–129), R040 mutant (pCMV-ayw Δ120–490), R041 (pCMV-ayw Δ490–827), R025 mutant (pCMV-ayw Δ827–1238), R026 mutant (pCMV-ayw Δ1238–1374), R027 mutant (pCMV-ayw Δ1374–1419), and R053 (pCMV-ayw Δ1419–1592).

In summary, the present invention reveals two novel cis-acting elements that are essential for the HBV genome replication. The complete mapping of cis-acting elements that are essential for HBV genome replication allowed us to design a prototype HBV vector.

EXAMPLE 5

Design of Prototype HBV Gene Therapy Vectors

Figure 6:
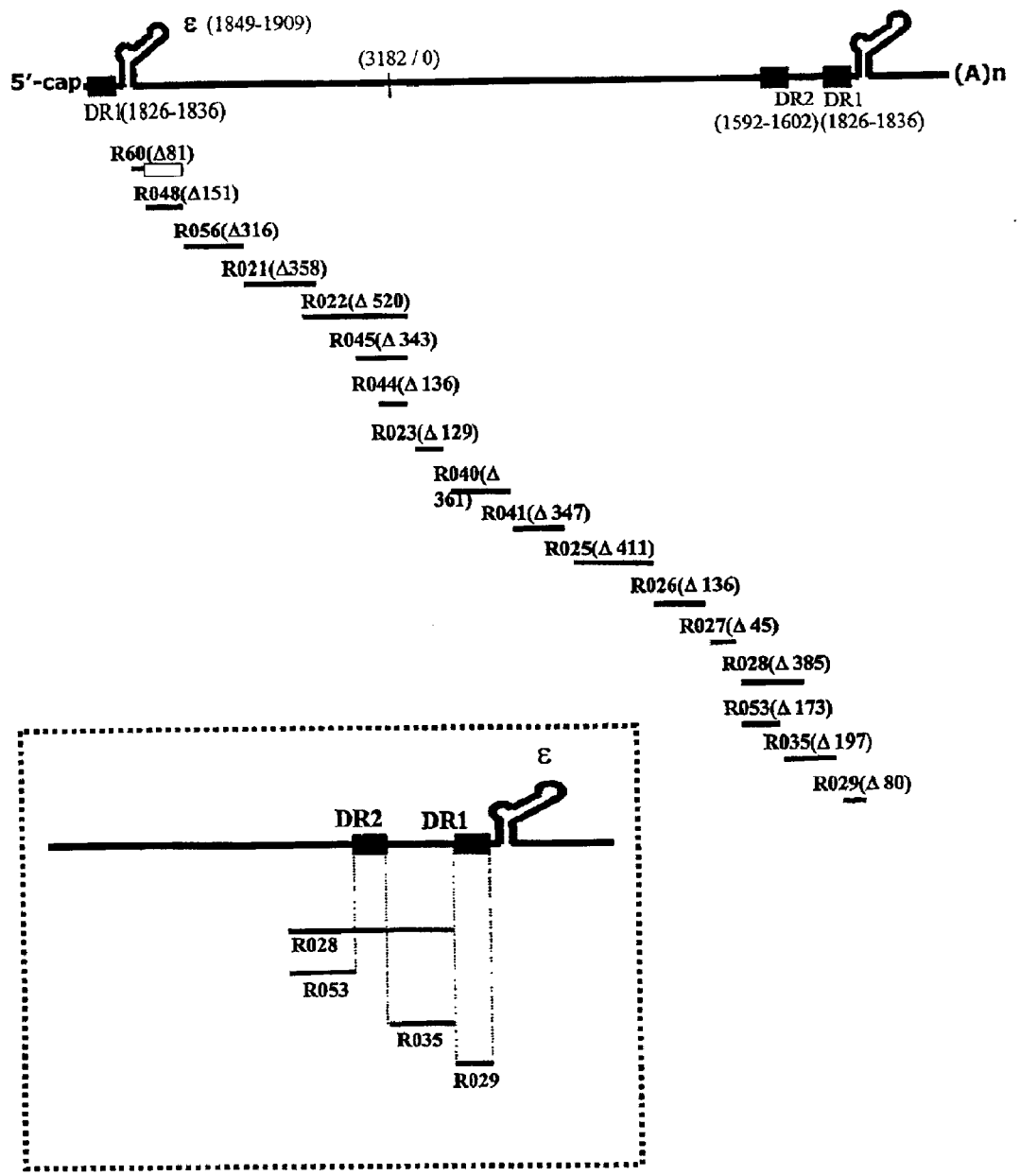
FIG. 6. Map of a series of small deletion mutants. The sequence deleted in each mutant was indicated by a solid line. The plasmid names are indicated by prefix R followed by numbers. The nucleotide position and the size of the deletions are indicated.
Figure 7:
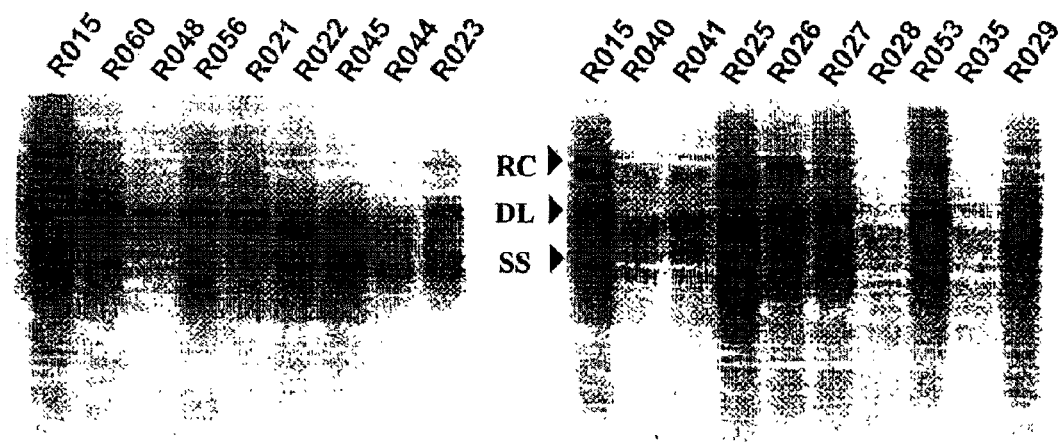
FIG. 7. An autoradiograph of Southern blot analysis of a series of deletion mutants to determine if each deletion mutant is replication-competent. RC, relaxed circular DNA; DL, double-stranded linear DNA; SS, single-stranded DNA.

The present invention reveals two novel cis-acting elements that are essential for the HBV genome replication. In literature, a half dozen elements have been reported to be essential in various stages of HBV genome synthesis. Among these are: 5'-epsilon for encapsidation (Hirsh et al., 1991; Junker-Niepmann et al., 1990), DR2 element (Condreay et al., 1992; Loeb et al., 1996), DR1 element (Seeger et al., 1991), r (repeat) element for circularization (Loeb et al., 1997), and PRE element for post-transcriptional RNA processing (Yen, 1998). In addition to these, the two elements identified in the invention, termed α and β, complete the mapping of cis-acting elements essential for HBV viral genome replication (FIG. 6).

Based on the information on these cis-acting elements, a prototype HBV gene therapy vector was designed (FIG. 8). The critical parameters of this gene therapy vector are the size and position of the inserts. In this prototype vector, two insertion sites were identified. First, the sequence (nt 1909–2816) between 5' epsilon and the α element could be substituted by a heterologous gene of interest. At the very least, the 0.9 K bp fragment can be substituted in this site. Since this insertion site overlaps the core open reading frame, the core promoter can then be used to drive the heterologous gene inserted. Secondly, the sequence (nt. 3052–1592) between α element and DR2 element can be substituted by a heterologous gene. A fragment up to 1.7 K bp can be substituted in this site. Similarly, this insertion site overlaps the pre-S2/S gene. Thus, the pre-S2/S promoter can be used to derive the heterologous gene inserted.

EXAMPLE 6

Construction of HBV Vector Containing a Heterologous Gene

Figure 9:
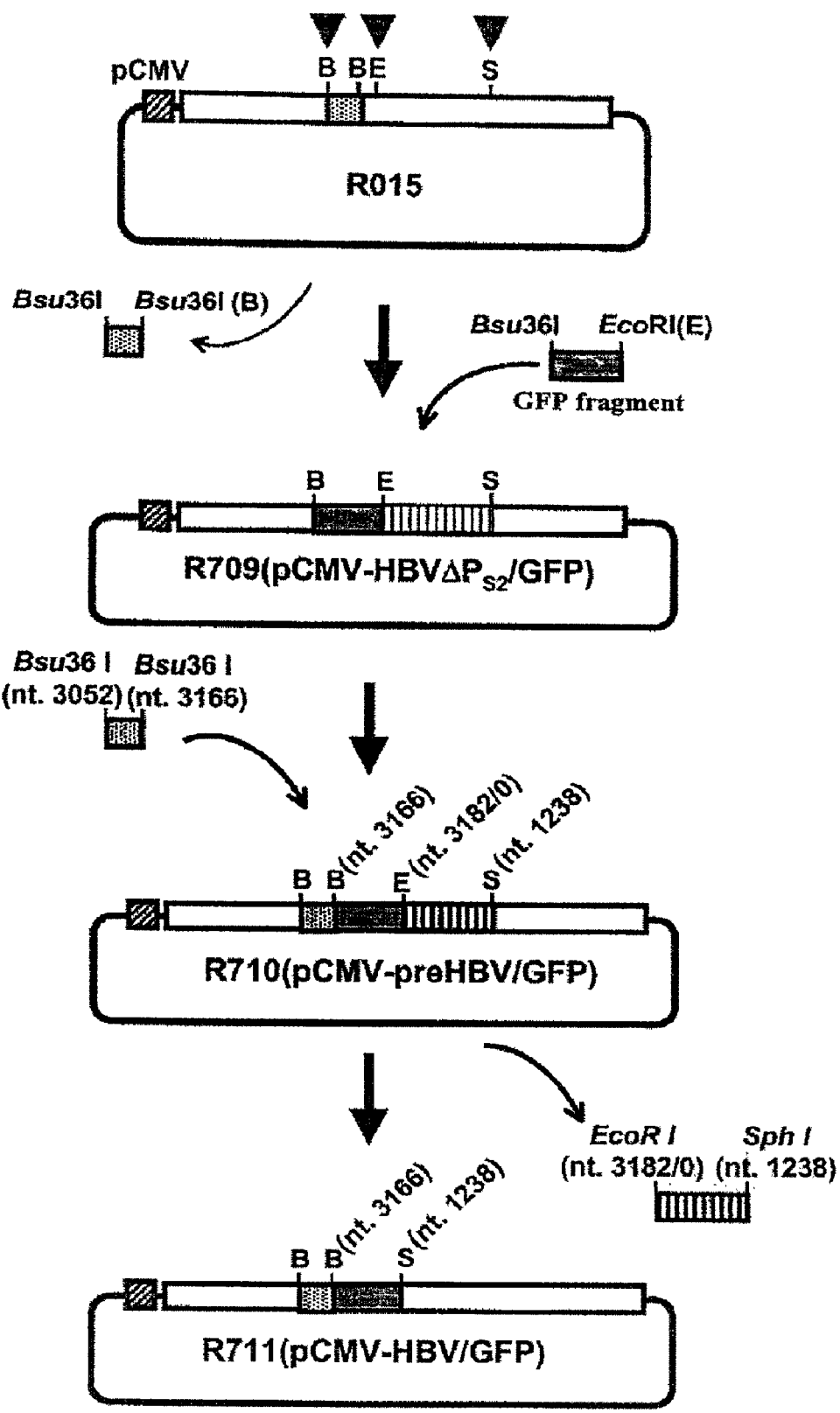
FIG. 9. A schematic representation of subcloning procedure of R711 plasmid.

To test feasibility of the prototype vector described in EXAMPLE 5, a HBV vector was made by the insertion of GFP (green fluorescent protein) gene at the site proposed: R711 (pCMV-HBV/GFP) (FIG. 9).

6-1. The Insertion Site and the Promoter

The insertion site was determined by considering following points: (i) all cis-acting elements essential for HBV genome replication should be kept intact, (ii) the endogenous viral promoter needs to be employed to maximize the coding capacity of the vector without exceeding the maximal packaging limit.

6-2. Insertion of GFP (Green Fluorescent Protein) Gene into the HBV Vector

Insertion of the 0.7 K bp GFP fragment was facilitated by polymerase chain reaction (PCR). Restriction sites were created at the end of the PCR fragment by an appropriately designed PCR primer. First of all, R709 (pCMV-HBV/ΔPs2GFP) construct was made by substitution of Bsu36 I(nt. 3052)-to-EcoR I(nt. 3182) fragment of R015 with the 0.7 K bp Bsu36 I-to-EcoR I fragment of PCR product encoding the GFP (green fluorescent protein) gene. The primers used for PCR were:

GFPBsuFII;

5-GTCACT<u>CCTCAGG</u>CCATGAGTAAAGGAGAAG-3

Bsu36I

GFPEcoRII;

5-G<u>GAATTC</u>CTTATTTGTATAGTTCATC-3

EcoRI

In this subcloning process, a subset of the pre-S2/S promoter was deleted. To make up this deletion, the Bsu36 I(nt. 3052)-to-Bsu36 I(nt. 3166) fragment was inserted into R709 plasmid to create R710 (pCMV-preHBV/GFP). Subsequently, to construct R711 (pCMV-HBV/GPF), the EcoR I(nt. 3182)-to-Sph I(nt. 1238) fragment was deleted by restriction digestion. Taken together, the 1.3 K bp fragment (EcoR I-to-Sph I) of HBV genome was substituted by the 0.7 K bp GFP fragment. Thus, the size of the genome is approximately 0.6 K bp smaller than the wild-type.

EXAMPLE 7

Confirmation of Replication Competency of the Recombinant HBV Vector

Figure 10:
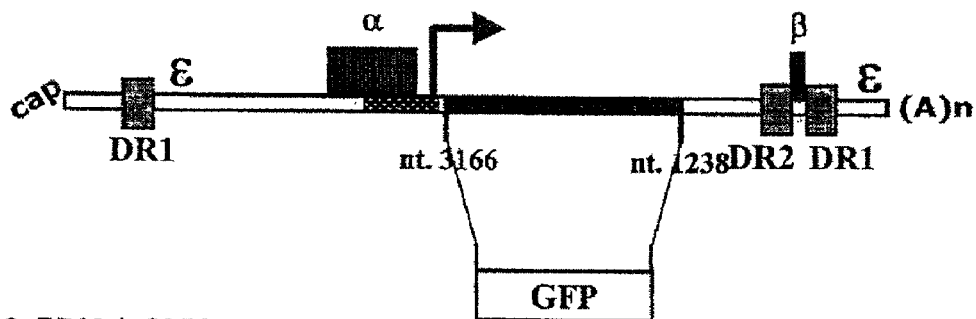
FIG. 10. A schematic representation of R711 plasmid with cis-acting elements.
Figure 10:
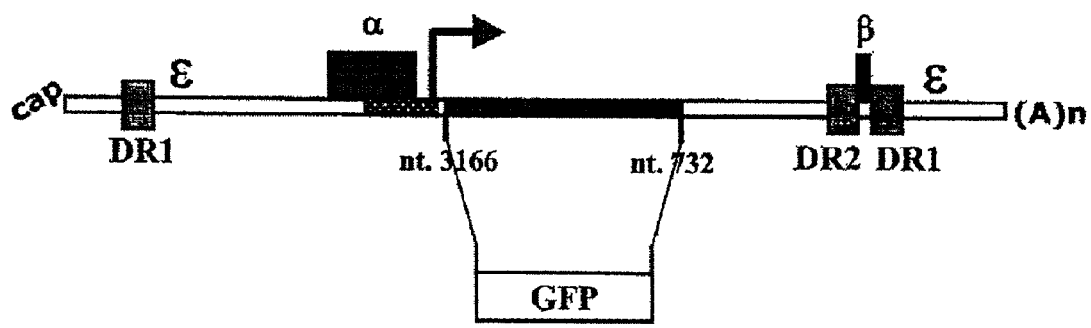
Figure 10:
Figure 10:
Figure 10:
Figure 10:
Figure 10:

Feasibility of the recombinant HBV vector was examined by testing replication competency of the HBV vector. Huh7 cells were transfected by R711 plasmid, along with a helper, pCMV-CPS. DNA extraction and Southern blots were performed as described in EXAMPLE 2-2. DNA extracted from HepG2 2.2.15 cells was included as a control (Sells et al., 1988). FIG. 10a indicated that RC DNA was detected from cells transfected by R711. Further, the amount of RC DNA and the relative amount of three species of replication-intermediate DNA was comparable to that of R015, the wild-type HBV clone. In addition, the replication of the HBV-GFP vector was further confirmed by using GFP probe (FIG. 10b).

All publications and patent applications cited in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not to be unduly limited to such specific embodiments. Indeed, various modifications of the described modes for carrying out the invention which are obvious to those skilled in molecular biology or related fields are intended to be within the scope of the following claims.

OTHER PUBLICATIONS

Anderson, W. F, Science 256:808–813(1992).
Ausubel, F. et al. eds., *Current Protocols in Molecular Biology*, Wiley and Sons, New York, 1995.
Chaisomchit, S., D. L. J. Tyrrell, and L. J. Chang. Gene Therapy 4:1330–1340(1997).
Chiang. P. W., K. S. Jeng, C. P. Hu, and C. M. Chang. Virology 186:701–711(1992).
Condreay, L. D., T. T. Wu, C. E. Aldrich, M. A. Delaney, J. Summers, C. Seeger, and W. S. Mason. Virology 188:208–216(1992).
Crystal, R. G. Science 270:404–410(1995).
Douglas, J. T., R. C. Miller, M. Kim, I. Dmitriev, G. Mikheeva, V. Krasnykh, and D. T. Curiel. Nature Biotechnology 17: 470–475(1999).
Friedmann, T. ed. Cold Spring Harbor Laboratory Press, Cold Spring Harbor, N.Y., 1999.
Galibert, F., E. Mandart., F. Fitoussi, P. Tiollais, and P. Charnay. Nature 28: 646–650(1979).
Ganem, D., and H. E. Varmus. Annu. Rev. Biochem. 56:651–593(1987).
Ganem, D., "Hepadnaviridae and Their Replication," in *Fundamental Virology*, 3rd edition, Fields, B. N., et al., eds, Lippincott-Raven Press, Philadelphia, 1996.
Havert, M., and D. L. Loeb. J. Virol. 71: 5336–5344(1997).
Hirsch, R. C., D. D. Loeb, J. R. Pollack, and D. Ganem. J. Virol. 65: 3309–3316(1991).
Ho, T.-C., K.-S. Jeng, C.-P. Hu and C. Chang. J. Virol. 74: 9010–9018(2000).
Huang, Z., and T. S. B. Yen. Mol. Cell. Biol. 15: 3864–3869 (1995).
Jeong, J.-K. , G.-S. Yoon, and W.-S. Ryu. J. Virol. 74:5502–5508(2000)
Junker-Niepmann, M., R. Bartenschlager, and H. Schaller. EMBO J. 9:3389–3396(1990).
Loeb, D. D., R. C. Hirsh, and D. Ganem. EMBO J. 10:3533–3540(1991).
Loeb, D. D., and R. Tian. J. Virol. 69: 686–6891(1995).
Loeb., D. D., R. Tian, and K. Gulya. J. Virol. 70: 8684–8690 (1996).
Loeb., D. D., K. Gulya. and R. Tian J. Virol. 71: 152–160 (1997).
Mulligan, R. C., Science 260: 926–932(1993).
Nassal, M., Junker-Niepmann, and H. Schaller. Cell 63: 1357–1363(1990).
Nassal, M., and A. Rieger. J. Virol. 70:2764–2773(1996).
Nassal, M., H. Schaller. J. Viral Hepatitis 3: 217–226(1996).
Pollack, J. R., and D. Ganem. J. Virol. 68:5579–5587(1994).
Protzer, U., M. Nassal., P.-W. Chiang, M. Kirschfink, and H. Schaller. Proc. Natl. Acad. Sci. USA 96:10818–10823 (1999)
Sambrook et al., in *Molecular Cloning: A Laboratory Manual*, Cold Spring Harbor Laboratory Press, 3rd Ed, Cold Spring Harbor (2001).
Sells, M. A., A. Z. Zelent, M. Shvartsman, and G. Acs. J. Virol. 62: 2836–2844(1988).
Seeger, C. and J. Maragos. J. Virol. 65:5190–5195(1991).
Shih, C. L., S. Li, S. Roychoudhury, and M. H. Ho. Proc. Natl. Acad. Sci. USA 86:6323–6327(1989)
Staprans, S., D. D. Loeb., and D. Ganem. J. Virol. 65: 1255–1262(1991).
Wang, G. H., and C. Seeger. Cell 71:663–670(1992).
Wang, G. H., and C. Seeger. J. Virol. 67:6507–6512(1993).
Yang, Y., and J. M. Wilson. J. Immunol. 155:2564–2570 (1995).
Yen., T. S. B. Semin. Virol. 8:319–328(1998).

What is claimed is:

1. A prototype hepatitis B virus vector comprising two novel cis-acting elements essential for hepatitis B virus genome replication, consisting of an α element and a β element, whose nucleotide sequences are described in SEQ ID 1 and 2, respectively.

2. The prototype hepatitis B virus vector of claim 1, wherein said nucleotide sequence is described in SEQ ID 3, comprising, in the 5' to 3' direction, the cytomegalovirus immediate early promoter, the DR1, the epsilon, the α element, the DR2, the β element, and the DR1 element.

3. The prototype hepatitis B virus vector of claim 2, wherein said insertion site is selected between the 5' epsilon and the α element.

4. The prototype hepatitis B virus vector of claim 2, wherein said the insertion site is selected between the α element and the DR2.

5. The prototype hepatitis B virus vector of claim 2, wherein said vector further comprises an endogenous viral promoter.

6. The prototype hepatitis B virus vector of claim 5, wherein said viral promoter is selected from the group consisting of the core promoter and the pre-S2/S promoter, respectively.

7. The prototype hepatitis B virus vector of claim 2, wherein said nucleotide sequences up to 0.90 K bp can be inserted between the 5' epsilon and the α element without exceeding the wild-type genome size of the 3.2 K bp.

8. The prototype hepatitis B virus vector of claim 2, wherein said nucleotide sequences up to 1.7 K bp can be inserted between the α element and DR2 element without exceeding the wild-type genome size of the 3.2 K bp.

9. The prototype hepatitis B virus vector of claim 2, wherein said vector is replication defective.

10. The vector of claim 1 comprising heterologous sequences which express at least one functional heterologous gene product.

* * * * *

SEQUENCE LISTING

<160> NUMBER OF SEQ ID NOS: 5

<210> SEQ ID NO 1
<211> LENGTH: 235
<212> TYPE: DNA
<213> ORGANISM: HBV
<220> FEATURE:
<221> NAME/KEY: gene
<222> LOCATION: (1)..(235)
<223> OTHER INFORMATION: Alpha-element of HBV

<400> SEQUENCE: 1

```
gtcaccatat tcttgggaac aagatctaca gcatggggca gaatctttcc accagcaatc      60
ctctgggatt ctttcccgac caccagttgg atccagcctt cagagcaaac accgcaaatc     120
cagattggga cttcaatccc aacaaggaca cctggccaga cgccaacaag gtaggagctg     180
gagcattcgg gctgggtttc accccaccgc acggaggcct tttggggtgg agccc          235
```

<210> SEQ ID NO 2
<211> LENGTH: 197
<212> TYPE: DNA
<213> ORGANISM: HBV
<220> FEATURE:
<221> NAME/KEY: gene
<222> LOCATION: (1)..(197)
<223> OTHER INFORMATION: Beta- element of HBV

<400> SEQUENCE: 2

```
gcatggagac caccgtgaac gcccaccaaa tattgcccaa ggtcttacat aagaggactc      60
ttggactctc agcaatgtca acgaccgacc ttgaggcata cttcaaagac tgtttgttta     120
aagactggga ggagttgggg gaggagatta ggttaaaggt ctttgtacta ggaggctgta     180
ggcataaatt ggtctgc                                                    197
```

<210> SEQ ID NO 3
<211> LENGTH: 8007
<212> TYPE: DNA
<213> ORGANISM: HBV
<220> FEATURE:
<221> NAME/KEY: gene
<222> LOCATION: (1)..(8007)
<223> OTHER INFORMATION: Prototype vector of HBV

<400> SEQUENCE: 3

```
aacttttcca cctctgccta atcatctctt gttcatgtcc tactgttcaa gcctccaagc      60
tgtgccttgg gtggctttgg ggcatggaca tcgacccctta taaagaattt ggagctactg    120
tggagttact ctcgttttg ccttctgact tctttccttc agtacgagat cttctagata      180
ccgcctcagc tctgtatcgg gaagccttag agtctcctga gcattgttca cctcaccata     240
ctgcactcag gcaagcaatt ctttgctggg ggaactaat gactctagct acctgggtgg     300
gtgttaattt ggaagatcca gcgtctagag acctagtagt cagttatgtc aacactaata    360
tgggcctaaa gttcaggcaa ctcttgtggt ttcacatttc ttgtctcact tttggaagag    420
aaacagttat agagtatttg gtgtctttcg gagtgtggat tcgcactcct ccagcttata    480
gaccaccaaa tgcccctatc ctatcaacac ttccggagac tactgttgtt agacgacgag    540
gcaggtcccc tagaagaaga actccctcgc ctcgcagacg aaggtctcaa tcgccgcgtc    600
gcagaagatc tcaatctcgg gaatctcaat gttagtattc cttggactca taaggtgggg    660
aactttactg ggctttattc ttctactgta cctgtcttta atcctcattg gaaaacacca    720
```

```
tcttttccta atatacattt acaccaagac attatcaaaa aatgtgaaca gtttgtaggc    780
ccactcacag ttaatgagaa agaagattg caattgatta tgcctgccag gttttatcca    840
aaggttacca aatatttacc attggataag ggtattaaac cttattatcc agaacatcta    900
gttaatcatt acttccaaac tagacactat ttacacactc tatggaaggc gggtatatta    960
tataagagag aaacaacaca tagcgcctca ttttgtgggt caccatattc ttgggaacaa   1020
gatctacagc atgggcaga atctttccac cagcaatcct ctgggattct ttcccgacca   1080
ccagttggat ccagccttca gagcaaacac cgcaaatcca gattgggact tcaatcccaa   1140
caaggacacc tggccagacg ccaacaaggt aggagctgga gcattcgggc tgggtttcac   1200
cccaccgcac ggaggccttt tggggtggag ccctcaggct cagggcatac tacaaacttt   1260
gccagcaaat ccgcctcctg cctccaccaa tcgccagtca ggaaggcagc ctacccccgct  1320
gtctccacct ttgagaaaca ctcatcctca ggccatgcag tggaattcca caaccttcca   1380
ccaaactctg caagatccca gagtgagagg cctgtatttc cctgctggtg ctccagttc    1440
aggaacagta aaccctgttc tgactactgc ctctccctta tcgtcaatct tctcgaggat   1500
tggggaccct gcgctgaaca tggagaacat cacatcagga ttcctaggac cccttctcgt   1560
gttacaggcg gggttttttct tgttgacaag aatcctcaca ataccgcaga gtctagactc   1620
gtggtggact tctctcaatt ttctagggg aactaccgtg tgtcttggcc aaaattcgca   1680
gtccccaacc tccaatcact caccaacctc ttgtcctcca acttgtcctg gttatcgctg   1740
gatgtgtctg cggcgtttta tcatcttcct cttcatcctg ctgctatgcc tcatcttctt   1800
gttggttctt ctggactatc aaggtatgtt gcccgtttgt cctctaattc caggatcctc   1860
aacaaccagc acgggaccat gccggacctg catgactact gctcaaggaa cctctatgta   1920
tccctcctgt tgctgtacca aaccttcgga cggaaattgc acctgtattc ccatcccatc   1980
atcctgggct ttcggaaaat tcctatggga gtgggcctca gcccgtttct cctggctcag   2040
tttactagtg ccatttgttc agtggttcgt agggctttcc cccactgttt ggctttcagt   2100
tatatggatg atgtggtatt gggggccaag tctgtacagc atcttgagtc ccttttacc    2160
gctgttacca attttctttt gtctttgggt atacatttaa accctaacaa acaaagaga    2220
tggggttact ctctaaattt tatgggttat gtcattggat gttatgggtc cttgccacaa   2280
gaacacatca tacaaaaaat caaagaatgt tttagaaaac ttcctattaa caggcctatt   2340
gattggaaag tatgtcaacg aattgtgggt cttttgggtt ttgctgcccc ttttacacaa   2400
tgtggttatc ctgcgttgat gcctttgtat gcatgtattc aatctaagca ggctttcact   2460
ttctcgccaa cttacaaggc ctttctgtgt aaacaatacc tgaacccttta ccccgttgcc   2520
cggcaacggc caggtctgtg ccaagtgttt gctgacgcaa cccccactgg ctggggcttg   2580
gtcatgggcc atcagcgcat gcgtggaacc ttttcggctc ctctgccgat ccatactgcg   2640
gaactcctag ccgcttgttt tgctcgcagc aggtctggag caaacattat cgggactgat   2700
aactctgttg tcctatcccg caaatataca tcgtttccat ggctgctagg ctgtgctgcc   2760
aactggatcc tgcgcgggac gtcctttgtt tacgtcccgt cggcgctgaa tcctgcggac   2820
gacccttctc ggggtcgctt gggactctct cgtccccttc tccgtctgcc gttccgaccg   2880
accacgggcc gcacctctct ttacgcggac tcccgtctg tgccttctca tctgccggac   2940
cgtgtgcact tcgcttcacc tctgcacgtc gcatggagac caccgtgaac gcccaccaaa   3000
tattgcccaa ggtcttacat aagaggactc ttggactctc agcaatgtca acgaccgacc   3060
```

```
ttgaggcata cttcaaagac tgtttgttta aagactggga ggagttgggg gaggagatta      3120
ggttaaaggt cttttgtacta ggaggctgta ggcataaatt ggtctgcgca ccagcaccat     3180 gcaactttt cacctctgcc taatcatctc ttgttcatgt cctactgttc aagcctccaa       3240
gctgtgcctt gggtggcttt ggggcatgga catcgaccct tataaagaat ttggagctac     3300
tgtggagtta ctctcgtttt tgccttctga cttctttcct tcagtacgag atcttctaga     3360 gggcccctatt ctatagtgtc acctaaatgc tagaggatct ttgtgaagga accttacttc    3420
tgtggtgtga cataattgga caaactacct acagagattt aaagctctaa ggtaaatata     3480
aaatttttaa gtgtataatg tgttaaacta ctgattctaa ttgtttgtgt attttagatt     3540
ccaacctatg gaactgatga atgggagcag tggtggaatg cctttaatga ggaaaacctg     3600
ttttgctcag aagaaatgcc atctagtgat gatgaggcta ctgctgactc tcaacattct     3660
actcctccaa aaagaagag aaaggtagaa gaccccaagg actttccttc agaattgcta      3720
agttttttga gtcatgctgt gtttagtaat agaactcttg cttgctttgc tatttacacc     3780
acaaaggaaa aagctgcact gctatacaag aaaattatgg aaaaatattt gatgtatagt    3840
gccttgacta gagatcataa tcagccatac cacatttgta gaggttttac ttgctttaaa    3900
aaacctccca cacctccccc tgaacctgaa acataaaatg aatgcaattg ttgttgttaa    3960
cttgtttatt gcagcttata atggttacaa ataaagcaat agcatcacaa atttcacaaa    4020
taaagcattt ttttcactgc attctagttg tggtttgtcc aaactcatca atgtatctta    4080
tcatgtctgg atcatcccgc catggtatca acgccatatt tctatttaca gtagggacct   4140
cttcgttgtg taggtaccgc tgtattccta gggaaatagt agaggcacct tgaactgtct    4200
gcatcagcca tatagccccc gctgttcgac ttacaaacac aggcacagta ctgacaaacc    4260
catacacctc ctctgaaata cccatagttg ctagggctgt ctccgaactc attacaccct    4320
ccaaagtcag agctgtaatt tcgccatcaa gggcagcgag ggcttctcca gataaaatag    4380
cttctgccga gagtcccgta agggtagaca cttcagctaa tccctcgatg aggtctacta    4440
gaatagtcag tgcggctccc attttgaaaa ttcacttact tgatcagctt cagaagatgg    4500
cggagggcct ccaacacagt aattttcctc ccgactctta aaatagaaaa tgtcaagtca    4560
gttaagcagg aagtggacta actgacgcag ctggccgtgc gacatcctct tttaattagt    4620
tgctaggcaa cgccctccag agggcgtgtg gttttgcaag aggaagcaaa agcctctcca    4680
cccaggccta gaatgtttcc acccaatcat tactatgaca acagctgttt tttttagtat    4740
taagcagagg ccggggaccc ctgggccggc ccgcttactc tggagaaaaa gaagagaggc    4800
attgtagagg cttccagagg caacttgtca aaacaggact gcttctattt ctgtcacact    4860
gtctggccct gtcacaaggt ccagcacctc cataccccct ttaataagca gtttgggaac    4920
gggtgcgggt cttactccgc ccatcccgcc cctaactccg cccagttccg cccattctcc    4980
gccccatggc tgactaattt tttttattta tgcagaggcc gaggccgcct cggcctctga    5040
gctattccag aagtagtgag gaggcttttt tggaggccta ggcttttgca aaaagctaat    5100
tcggcgtaat ctgctgcttg caaacaaaaa accaccgct accagcggtg gtttgtttgc     5160
cggatcaaga gctaccaact cttttccga aggtaactgg cttcagcaga gcgcagatac     5220
caaatactgt ccttctagtg tagccgtagt taggccacca cttcaagaac tctgtagcac    5280
cgcctacata cctcgctctg ctaatcctgt taccagtggc tgctgccagt ggcgataagt    5340
cgtgtcttac cgggttggac tcaagacgat agttaccgga taaggcgcag cggtcgggct    5400 gaacggggg ttcgtgcaca cagcccagct tggagcgaac gacctacacc gaactgagat     5460
```

-continued

```
acctacagcg tgagcattga gaaagcgcca cgcttcccga agggagaaag gcggacaggt    5520
atccggtaag cggcagggtc ggaacaggag agcgcacgag ggagcttcca gggggaaacg    5580
cctggtatct ttatagtcct gtcgggtttc gccacctctg acttgagcgt cgattttgt    5640 gatgctcgtc agggggcgg agcctatgga aaaacgccag caacgcaagc tagcttctag     5700
ctagaaattg taaacgttaa tattttgtta aaattcgcgt taaattttg ttaaatcagc      5760 tcatttttta accaataggc cgaaatcggc aaaatccctt ataaatcaaa agaatagccc    5820
gagatagggt tgagtgttgt tccagtttgg aacaagagtc cactattaaa gaacgtggac    5880
tccaacgtca aagggcgaaa aaccgtctat cagggcgatg gcccgccact acgtgaacca    5940
tcacccaaat caagtttttt ggggtcgagg tgccgtaaag cactaaatcg aaccctaaa     6000 gggagccccc gatttagagc ttgacgggga agccggcga acgtggcgag aaaggaaggg     6060
aagaaagcga aaggagcggg cgctagggcg ctggcaagtg tagcggtcac gctgcgcgta    6120
accaccacac ccgccgcgct taatgcgccg ctacagggcg cgtactatgg ttgctttgac    6180
gagaccgtat aacgtgcttt cctcgttgga atcagagcgg gagctaaaca ggaggccgat    6240
taaagggatt ttagacagga acggtacgcc agctggatta ccaaagggcc tcgtgatacg    6300
cctattttta taggttaatg tcatgataat aatggtttct tagacgtcag gtggcacttt    6360
tcggggaaat gtgcgcggaa cccctatttg tttatttttc taaatacatt caaatatgta    6420
tccgctcatg agacaataac cctgataaat gcttcaataa tattgaaaaa ggaagagtat    6480
gagtattcaa catttccgtg tcgcccttat tcccttttt gcggcatttt gccttcctgt     6540
ttttgctcac ccagaaacgc tggtgaaagt aaaagatgct gaagatcagt tgggtgcacg    6600
agtgggttac atcgaactgg atctcaacag cggtaagatc cttgagagtt ttcgccccga    6660
agaacgtttt ccaatgatga gcacttttaa agttctgcta tgtggcgcgg tattatcccg    6720
tgttgacgcc gggcaagagc aactcggtcg ccgcatacac tattctcaga atgacttggt    6780
tgagtactca ccagtcacag aaaagcatct tacggatggc atgacagtaa gagaattatg    6840
cagtgctgcc ataaccatga gtgataacac tgcggccaac ttacttctga caacgatcgg    6900
aggaccgaag gagctaaccg ctttttttgca caacatgggg gatcatgtaa ctcgccttga    6960
tcgttgggaa ccggagctga atgaagccat accaaacgac gagcgtgaca ccacgatgcc    7020
tgcagcaatg gcaacaacgt tgcgcaaact attaactggc gaactactta ctctagcttc    7080
ccggcaacaa ttaatagact ggatggaggc ggataaagtt gcaggaccac ttctgcgctc    7140
ggcccttccg gctggctggt ttattgctga taaatctgga gccggtgagc gtgggtctcg    7200
cggtatcatt gcagcactgg ggccagatgg taagccctcc cgtatcgtag ttatctacac    7260
gacggggagt caggcaacta tggatgaacg aaatagacag atcgctgaga taggtgcctc    7320
actgattaag cattggtaac tgtcagacca agtttactca tatatacttt agattgattt    7380
aaaacttcat ttttaatttc tctagcgcgt tgacattgat tattgactag ttattaatag    7440
taatcaatta cggggtcatt agttcatagc ccatatatgg agttccgcgt tacataactt    7500
acggtaaatg gcccgcctgg ctgaccgccc aacgacccc gcccattgac gtcaataatg     7560
acgtatgttc ccatagtaac gccaataggg actttccatt gacgtcaatg ggtggactat    7620
ttacggtaaa ctgcccactt ggcagtacat caagtgtatc atatgccaag tacgccccct    7680
attgacgtca atgacggtaa atggcccgcc tggcattatg cccagtacat gaccttatgg    7740
gactttccta cttggcagta catctacgta ttagtcatcg ctattaccat ggtgatgcgg    7800
```

-continued

| | |
|---|---|
| ttttggcagt acatcaatgg gcgtggatag cggtttgact cacgggggatt tccaagtctc | 7860 |
| cacccattg acgtcaatgg gagtttgttt tggcaccaaa atcaacggga ctttccaaaa | 7920 |
| tgtcgtaaca actccgcccc attgacgcaa atgggcggta ggcgtgtacg gtgggaggtc | 7980 |
| tatataagca gagctctctg gctaact | 8007 |

<210> SEQ ID NO 4
<211> LENGTH: 8717
<212> TYPE: DNA
<213> ORGANISM: Artificial Sequence
<220> FEATURE:
<223> OTHER INFORMATION: R711: pCMV-HBV/GFP Full Sequence

<400> SEQUENCE: 4

| | |
|---|---|
| aacttttttca cctctgccta atcatctctt gttcatgtcc tactgttcaa gcctccaagc | 60 |
| tgtgccttgg gtggctttgg ggcatggaca tcgacccttta taagaatttt ggagctactg | 120 |
| tggagttact ctcgtttttg ccttctgact tctttccttc agtacgagat cttctagata | 180 |
| ccgcctcagc tctgtatcgg gaagccttag agtctcctga gcattgttca cctcaccata | 240 |
| ctgcactcag gcaagcaatt ctttgctggg ggaactaat gactctagct acctgggtgg | 300 |
| gtgttaattt ggaagatcca gcgtctagag acctagtagt cagttatgtc aacactaata | 360 |
| tgggcctaaa gttcaggcaa ctcttgtggt ttcacatttc ttgtctcact tttggaagag | 420 |
| aaacagttat agagtatttg gtgtctttcg gagtgtggat tcgcactcct ccagcttata | 480 |
| gaccaccaaa tgcccctatc ctatcaacac ttccggagac tactgttgtt agacgacgag | 540 |
| gcaggtcccc tagaagaaga actccctcgc ctcgcagacg aaggtctcaa tcgccgcgtc | 600 |
| gcagaagatc tcaatctcgg gaatctcaat gttagtattc cttggactca taaggtgggg | 660 |
| aactttactg gcttttattc ttctactgta cctgtcttta atcctcattg gaaaacacca | 720 |
| tcttttccta atatacattt acaccaagac attatcaaaa aatgtgaaca gtttgtaggc | 780 |
| ccactcacag ttaatgagaa aagaagattg caattgatta tgcctgccag ttttatcca | 840 |
| aaggttacca aatatttacc attggataag ggtattaaac cttattatcc agaacatcta | 900 |
| gttaatcatt acttccaaac tagacactat ttacacactc tatggaaggc gggtatatta | 960 |
| tataagagag aaacaacaca tagcgcctca ttttgtgggt caccatattc ttgggaacaa | 1020 |
| gatctacagc atggggcaga atctttccac cagcaatcct ctgggattct ttcccgacca | 1080 |
| ccagttggat ccagccttca gagcaaacac cgcaaatcca gattgggact tcaatcccaa | 1140 |
| caaggacacc tggccagacg ccaacaaggt aggagctgga gcattcgggc tgggttttcac | 1200 |
| cccaccgcac ggaggccttt tggggtggag ccctcaggct cagggcatac tacaaacttt | 1260 |
| gccagcaaat ccgcctcctg cctccaccaa tcgccagtca ggaaggcagc ctaccccgct | 1320 |
| gtctccacct ttgagaaaca ctcatcctca ggagatgagt aaaggagaag aacttttcac | 1380 |
| tggagttgtc ccaattcttg ttgaattaga tggtgatgtt aatgggcaca atttttctgt | 1440 |
| cagtggagag ggtgaaggtg atgcaacata cggaaaactt acccttaaat ttatttgcac | 1500 |
| tactggaaaa ctacctgttc catggccaac acttgtcact actttctctt atggtgttca | 1560 |
| atgcttttca agatacccag atcatatgaa acagcatgac ttttttcaaga gtgccatgcc | 1620 |
| cgaaggttat gtacaggaaa gaactatatt tttcaaagat gacgggaact acaagacacg | 1680 |
| tgctgaagtc aagtttgaag gtgataccct tgttaataga atcgagttaa aggtattga | 1740 |
| ttttaaagaa gatggaaaca ttcttggaca caaattggaa tacaactata actcacacaa | 1800 |
| tgtatacatc atggcagaca acaaaagaa tggaatcaaa gttaacttca aaattagaca | 1860 |

```
caacattgaa gatggaagcg ttcaactagc agaccattat caacaaaata ctccaattgg    1920
cgatggccct gtccttttac cagacaacca ttacctgtcc acacaatctg cccttttcgaa   1980 agatcccaac gaaaagagag accacatggt ccttcttgag tttgtaacag ctgctgggat    2040
tacacatggc atggatgaac tatacaaata aggaattcca caaccttcca ccaaactctg    2100
caagatccca gagtgagagg cctgtatttc cctgctggtg gctccagttc aggaacagta    2160
aaccctgttc tgactactgc ctctccctta tcgtcaatct tctcgaggat tggggaccct    2220
gcgctgaaca tggagaacat cacatcagga ttcctaggac cccttctcgt gttacaggcg    2280 gggttttct  tgttgacaag aatcctcaca ataccgcaga gtctagactc gtggtggact    2340
tctctcaatt ttctaggggg aactaccgtg tgtcttggcc aaaattcgca gtccccaacc    2400
tccaatcact caccaacctc ttgtcctcca acttgtcctg gttatcgctg gatgtgtctg    2460
cggcgtttta tcatcttcct cttcatcctg ctgctatgcc tcatcttctt gttggttctt    2520
ctggactatc aaggtatgtt gcccgtttgt cctctaattc aggatcctc  aacaaccagc    2580 acgggaccat gccggacctg catgactact gctcaaggaa cctctatgta tccctcctgt    2640
tgctgtacca aaccttcgga cggaaattgc acctgtattc catcccatc  atcctgggct    2700 ttcgaaaaat tcctatggga gtgggcctca gcccgtttct cctggctcag tttactagtg    2760
ccatttgttc agtggttcgt agggctttcc cccactgttt ggctttcagt tatatggatg    2820
atgtggtatt gggggccaag tctgtacagc atcttgagtc ccttttttacc gctgttacca    2880 attttcttt  gtctttgggt atacatttaa accctaacaa acaaagagaa tggggttact    2940
ctctaaattt tatgggttat gtcattggat gttatgggtc cttgccacaa gaacacatca    3000
tacaaaaaat caaagaatgt tttagaaaac ttcctattaa caggcctatt gattggaaag    3060
tatgtcaacg aattgtgggt cttttgggtt ttgctgcccc ttttacacaa tgtggttatc    3120
ctgcgttgat gcctttgtat gcatgtattc aatctaagca ggctttcact ttctcgccaa    3180
cttacaaggc ctttctgtgt aaacaatacc tgaaccttta ccccgttgcc cggcaacggc    3240
caggtctgtg ccaagtgttt gctgacgcaa cccccactgg ctggggcttg gtcatgggcc    3300
atcagcgcat gcgtggaacc ttttcggctc ctctgccgat ccatactgcg gaactcctag    3360
ccgcttgttt tgctcgcagc aggtctggag caaacattat cgggactgat aactctgttg    3420
tcctatcccg caaatataca tcgtttccat ggctgctagg ctgtgctgcc aactggatcc    3480
tgcgcgggac gtccttttgtt tacgtcccgt cggcgctgaa tcctgcggac gacccttctc    3540
ggggtcgctt gggactctct cgtccccttc tccgtctgcc gttccgaccg accacggggc    3600
gcacctctct ttacgcggac tccccgtctg tgccttctca tctgccggac cgtgtgcact    3660
tcgcttcacc tctgcacgtc gcatggagac caccgtgaac gcccaccaaa tattgcccaa    3720
ggtcttacat aagaggactc ttggactctc agcaatgtca acgaccgacc ttgaggcata    3780
cttcaaagac tgtttgttta aagactggga ggagttgggg gaggagatta ggttaaaggt    3840
ctttgtacta ggaggctgta ggcataaatt ggtctgcgca ccagcaccat gcaactttt     3900 cacctctgcc taatcatctc ttgttcatgt cctactgttc aagcctccaa gctgtgcctt    3960
gggtggcttt gggcatggga catcgaccct tataaagaat ttggagctac tgtggagtta    4020
ctctcgtttt tgccttctga cttctttcct tcagtacgag atcttctaga gggcccctatt   4080 ctatagtgtc acctaaatgc tagaggatct ttgtgaagga accttacttc tgtggtgtga    4140
cataattgga caaactacct acagagattt aaagctctaa ggtaaatata aaattttaa     4200
```

```
gtgtataatg tgttaaacta ctgattctaa ttgtttgtgt attttagatt ccaacctatg      4260
gaactgatga atgggagcag tggtggaatg cctttaatga ggaaaacctg ttttgctcag      4320
aagaaatgcc atctagtgat gatgaggcta ctgctgactc tcaacattct actcctccaa      4380
aaaagaagag aaaggtagaa gaccccaagg actttccttc agaattgcta agttttttga      4440
gtcatgctgt gtttagtaat agaactcttg cttgctttgc tatttacacc acaaaggaaa      4500
aagctgcact gctatacaag aaaattatgg aaaaatattt gatgtatagt gccttgacta      4560
gagatcataa tcagccatac cacatttgta gaggttttac ttgctttaaa aaacctccca      4620
cacctccccc tgaacctgaa acataaaatg aatgcaattg ttgttgttaa cttgtttatt      4680
gcagcttata atggttacaa ataaagcaat agcatcacaa atttcacaaa taaagcattt      4740
ttttcactgc attctagttg tggtttgtcc aaactcatca atgtatctta tcatgtctgg      4800
atcatcccgc catggtatca acgccatatt tctatttaca gtagggacct cttcgttgtg      4860
taggtaccgc tgtattccta gggaaatagt agaggcacct tgaactgtct gcatcagcca      4920
tatagccccc gctgttcgac ttacaaacac aggcacagta ctgacaaacc catacacctc      4980
ctctgaaata cccatagttg ctaggctgt ctccgaactc attacaccct ccaaagtcag       5040
agctgtaatt tcgccatcaa gggcagcgag ggcttctcca gataaaatag cttctgccga      5100
gagtcccgta agggtagaca cttcagctaa tccctcgatg aggtctacta gaatagtcag      5160
tgcggctccc attttgaaaa ttcacttact tgatcagctt cagaagatgg cggagggcct      5220
ccaacacagt aatttttcctc ccgactctta aaatagaaaa tgtcaagtca gttaagcagg     5280
aagtggacta actgacgcag ctggccgtgc gacatcctct tttaattagt tgctaggcaa      5340
cgccctccag agggcgtgtg gttttgcaag aggaagcaaa agcctctcca cccaggccta      5400
gaatgtttcc acccaatcat tactatgaca acagctgttt ttttttagtat taagcagagg     5460 ccggggaccc ctgggccggc ccgcttactc tggagaaaaa gaagagaggc attgtagagg      5520
cttccagagg caacttgtca aaacaggact gcttctattt ctgtcacact gtctggccct      5580
gtcacaaggt ccagcacctc catacccct ttaataagca gtttgggaac gggtgcgggt       5640
cttactccgc ccatcccgcc cctaactccg cccagttccg cccattctcc gccccatggc      5700
tgactaattt ttttttattta tgcagaggcc gaggccgcct cggcctctga gctattccag      5760
aagtagtgag gaggcttttt tggaggccta ggcttttgca aaaagctaat tcggcgtaat      5820
ctgctgcttg caaacaaaaa aaccaccgct accagcggtg gtttgtttgc cggatcaaga      5880
gctaccaact ctttttccga aggtaactgg cttcagcaga gcgcagatac caaatactgt      5940
ccttctagtg tagccgtagt taggccacca cttcaagaac tctgtagcac cgcctacata      6000
cctcgctctg ctaatcctgt taccagtggc tgctgccagt ggcgataagt cgtgtcttac      6060
cgggttggac tcaagacgat agttaccgga taaggcgcag cggtcgggct gaacggggggg     6120 ttcgtgcaca cagcccagct tggagcgaac gacctacacc gaactgagat acctacagcg      6180
tgagcattga gaaagcgcca cgcttcccga agggagaaag gcggacaggt atccggtaag      6240
cggcagggtc ggaacaggag agcgcacgag ggagcttcca gggggaaacg cctggtatct      6300
ttatagtcct gtcgggtttc gccacctctg acttgagcgt cgatttttgt gatgctcgtc      6360 agggggggcgg agcctatgga aaaacgccag caacgcaagc tagcttctag ctagaaattg     6420
taaacgttaa tattttgtta aaattcgcgt taaattttt g ttaaatcagc tcattttta      6480 accaataggc cgaaatcggc aaaatccctt ataaatcaaa agaatagccc gagataggt       6540 tgagtgttgt tccagtttgg aacaagagtc cactattaaa gaacgtggac tccaacgtca      6600
```

```
aagggcgaaa aaccgtctat cagggcgatg gccgcccact acgtgaacca tcacccaaat    6660 caagttttt  ggggtcgagg tgccgtaaag cactaaatcg aaccctaaa  gggagccccc    6720 gatttagagc ttgacgggga aagccggcga acgtggcgag aaaggaaggg aagaaagcga    6780
aaggagcggg cgctagggcg ctggcaagtg tagcggtcac gctgcgcgta accaccacac    6840
ccgccgcgct taatgcgccg ctacagggcg cgtactatgg ttgctttgac gagaccgtat    6900
aacgtgcttt cctcgttgga atcagagcgg gagctaaaca ggaggccgat taaagggatt    6960
ttagacagga acggtacgcc agctggatta ccaaagggcc tcgtgatacg cctatttta    7020 taggttaatg tcatgataat aatggttct  tagacgtcag gtggcacttt tcggggaaat    7080
gtgcgcggaa cccctatttg tttatttttc taaatacatt caaatatgta tccgctcatg    7140
agacaataac cctgataaat gcttcaataa tattgaaaaa ggaagagtat gagtattcaa    7200
catttccgtg tcgcccttat cccttttttt gcggcatttt gccttcctgt ttttgctcac    7260
ccagaaacgc tggtgaaagt aaaagatgct gaagatcagt tgggtgcacg agtgggttac    7320
atcgaactgg atctcaacag cggtaagatc cttgagagtt ttcgccccga agaacgtttt    7380
ccaatgatga gcactttaa  agttctgcta tgtggcgcgg tattatcccg tgttgacgcc    7440
gggcaagagc aactcggtcg ccgcatacac tattctcaga atgacttggt tgagtactca    7500
ccagtcacag aaaagcatct tacggatggc atgacagtaa gagaattatg cagtgctgcc    7560
ataaccatga gtgataacac tgcggccaac ttacttctga caacgatcgg aggaccgaag    7620
gagctaaccg cttttttgca acatgggg  gatcatgtaa ctcgccttga tcgttgggaa    7680
ccggagctga atgaagccat accaaacgac gagcgtgaca ccacgatgcc tgcagcaatg    7740
gcaacaacgt tgcgcaaact attaactggc gaactactta ctctagcttc ccggcaacaa    7800
ttaatagact ggatggaggc ggataaagtt gcaggaccac ttctgcgctc ggcccttccg    7860
gctggctggt ttattgctga taaatctgga gccggtgagc gtgggtctcg cggtatcatt    7920
gcagcactgg ggccagatgg taagccctcc cgtatcgtag ttatctacac gacggggagt    7980
caggcaacta tggatgaacg aaatagacag atcgctgaga taggtgcctc actgattaag    8040
cattggtaac tgtcagacca agtttactca tatatacttt agattgattt aaaacttcat    8100
ttttaatttc tctagcgcgt tgacattgat tattgactag ttattaatag taatcaatta    8160
cggggtcatt agttcatagc ccatatatgg agttccgcgt tacataactt acggtaaatg    8220
gcccgcctgg ctgaccgccc aacgaccccc gcccattgac gtcaataatg acgtatgttc    8280
ccatagtaac gccaataggg actttccatt gacgtcaatg ggtggactat ttacggtaaa    8340
ctgcccactt ggcagtacat caagtgtatc atatgccaag tacgcccct  attgacgtca    8400 atgacggtaa atggcccgcc tggcattatg cccagtacat gaccttatgg actttcctta    8460
cttggcagta catctacgta ttagtcatcg ctattaccat ggtgatgcgg ttttggcagt    8520
acatcaatgg gcgtggatag cggtttgact cacggggatt tccaagtctc cacccattg    8580 acgtcaatgg gagtttgttt tggcaccaaa atcaacggga cttccaaaa  tgtcgtaaca    8640 actccgcccc attgacgcaa atgggcggta ggcgtgtacg gtgggaggtc tatataagca    8700
gagctctctg gctaact                                                   8717
```

<210> SEQ ID NO 5
<211> LENGTH: 7991
<212> TYPE: DNA
<213> ORGANISM: Artificial Sequence
<220> FEATURE:

<223> OTHER INFORMATION: R712: pCMV-HBV/GFP3.2 Full Sequence

<400> SEQUENCE: 5

| | | | | | |
|---|---|---|---|---|---|
| aactttttca | cctctgccta | atcatctctt | gttcatgtcc | tactgttcaa | gcctccaagc | 60 |
| tgtgccttgg | gtggctttgg | ggcatggaca | tcgaccctta | taaagaattt | ggagctactg | 120 |
| tggagttact | ctcgtttttg | ccttctgact | tctttccttc | agtacgagat | cttctagata | 180 |
| ccgcctcagc | tctgtatcgg | gaagccttag | agtctcctga | gcattgttca | cctcaccata | 240 |
| ctgcactcag | gcaagcaatt | ctttgctggg | gggaactaat | gactctagct | acctgggtgg | 300 |
| gtgttaattt | ggaagatcca | gcgtctagag | acctagtagt | cagttatgtc | aacactaata | 360 |
| tgggcctaaa | gttcaggcaa | ctcttgtggt | ttcacatttc | ttgtctcact | tttggaagag | 420 |
| aaacagttat | agagtatttg | gtgtctttcg | gagtgtggat | tcgcactcct | ccagcttata | 480 |
| gaccaccaaa | tgcccctatc | ctatcaacac | ttccggagac | tactgttgtt | agacgacgag | 540 |
| gcaggtcccc | tagaagaaga | actccctcgc | ctcgcagacg | aaggtctcaa | tcgccgcgtc | 600 |
| gcagaagatc | tcaatctcgg | gaatctcaat | gttagtattc | cttggactca | taaggtgggg | 660 |
| aactttactg | ggctttattc | ttctactgta | cctgtcttta | atcctcattg | gaaaacacca | 720 |
| tcttttccta | atatacattt | acaccaagac | attatcaaaa | aatgtgaaca | gtttgtaggc | 780 |
| ccactcacag | ttaatgagaa | aagaagattg | caattgatta | tgcctgccag | gttttatcca | 840 |
| aaggttacca | aatatttacc | attggataag | ggtattaaac | cttattatcc | agaacatcta | 900 |
| gttaatcatt | acttccaaac | tagacactat | ttacacactc | tatggaaggc | gggtatatta | 960 |
| tataagagag | aaacaacaca | tagcgcctca | ttttgtgggt | caccatattc | ttgggaacaa | 1020 |
| gatctacagc | atggggcaga | atcttttcca | cagcaatcct | ctgggattct | ttcccgacca | 1080 |
| ccagttggat | ccagccttca | gagcaaacac | cgcaaatcca | gattgggact | tcaatcccaa | 1140 |
| caaggacacc | tggccagacg | ccaacaaggt | aggagctgga | gcattcgggc | tgggtttcac | 1200 |
| cccaccgcac | ggaggccttt | tggggtggag | ccctcaggct | cagggcatac | tacaaacttt | 1260 |
| gccagcaaat | ccgcctcctg | cctccaccaa | tcgccagtca | ggaaggcagc | ctaccccgct | 1320 |
| gtctccacct | ttgagaaaca | ctcatcctca | ggagatgagt | aaaggagaag | aacttttcac | 1380 |
| tggagttgtc | ccaattcttg | ttgaattaga | tggtgatgtt | aatgggcaca | aattttctgt | 1440 |
| cagtggagag | ggtgaaggtg | atgcaacata | cggaaaactt | acccttaaat | ttatttgcac | 1500 |
| tactggaaaa | ctacctgttc | catggccaac | acttgtcact | actttctctt | atggtgttca | 1560 |
| atgcttttca | agatacccag | atcatatgaa | acagcatgac | ttttttcaaga | gtgccatgcc | 1620 |
| cgaaggttat | gtacaggaaa | gaactatatt | tttcaaagat | gacgggaact | acaagacacg | 1680 |
| tgctgaagtc | aagtttgaag | gtgataccct | tgttaataga | atcgagttaa | aggtattga | 1740 |
| ttttaaagaa | gatggaaaca | ttcttggaca | caaattggaa | tacaactata | actcacacaa | 1800 |
| tgtatacatc | atggcagaca | aacaaaagaa | tggaatcaaa | gttaacttca | aaattagaca | 1860 |
| caacattgaa | gatggaagcg | ttcaactagc | agaccattat | caacaaaata | ctccaattgg | 1920 |
| cgatggccct | gtccttttac | cagacaacca | ttacctgtcc | acacaatctg | ccctttcgaa | 1980 |
| agatcccaac | gaaaagagag | accacatggt | ccttcttgag | tttgtaacag | ctgctgggat | 2040 |
| tacacatggc | atggatgaac | tatacaaata | aggaattctt | cagttatatg | gatgatgtgg | 2100 |
| tattgggggc | caagtctgta | cagcatcttg | agtcccttt | taccgctgtt | accaattttc | 2160 |
| ttttgtcttt | gggtatacat | ttaaacccta | acaaaacaaa | gagatggggt | tactctctaa | 2220 |
| attttatggg | ttatgtcatt | ggatgttatg | ggtccttgcc | acaagaacac | atcatacaaa | 2280 |

-continued

```
aaatcaaaga atgttttaga aaacttccta ttaacaggcc tattgattgg aaagtatgtc    2340
aacgaattgt gggtcttttg ggttttgctg ccccttttac acaatgtggt tatcctgcgt    2400
tgatgccttt gtatgcatgt attcaatcta agcaggcttt cactttctcg ccaacttaca    2460
aggcctttct gtgtaaacaa tacctgaacc tttaccccgt tgcccggcaa cggccaggtc    2520
tgtgccaagt gtttgctgac gcaaccccca ctggctgggg cttggtcatg gccatcagc    2580 gcatgcgtgg aaccttttcg gctcctctgc cgatccatac tgcggaactc ctagccgctt    2640
gttttgctcg cagcaggtct ggagcaaaca ttatcgggac tgataactct gttgtcctat    2700
cccgcaaata tacatcgttt ccatggctgc taggctgtgc tgccaactgg atcctgcgcg    2760
ggacgtcctt tgtttacgtc ccgtcggcgc tgaatcctgc ggacgaccct tctcggggtc    2820
gcttgggact ctctcgtccc cttctccgtc tgccgttccg accgaccacg gggcgcacct    2880
ctctttacgc ggactcccg tctgtgcctt ctcatctgcc ggaccgtgtg cacttcgctt    2940
cacctctgca cgtcgcatgg agaccaccgt gaacgcccac caaatattgc caaggtctt    3000 acataagagg actcttggac tctcagcaat gtcaacgacc gaccttgagg catacttcaa    3060
agactgtttg tttaaagact gggaggagtt gggggaggag attaggttaa aggtctttgt    3120
actaggaggc tgtaggcata aattggtctg cgcaccagca ccatgcaact ttttcacctc    3180
tgcctaatca tctcttgttc atgtcctact gttcaagcct ccaagctgtg ccttgggtgg    3240
ctttggggca tggacatcga cccttataaa gaatttggag ctactgtgga gttactctcg    3300
tttttgcctt ctgacttctt tccttcagta cgagatcttc tagagggccc tattctatag    3360
tgtcacctaa atgctagagg atctttgtga aggaaccta cttctgtggt gtgacataat    3420
tggacaaact acctacagag attaaagct ctaaggtaaa tataaattt ttaagtgtat    3480 aatgtgttaa actactgatt ctaattgttt gtgtatttta gattccaacc tatggaactg    3540
atgaatggga gcagtggtgg aatgccttta atgaggaaaa cctgttttgc tcagaagaaa    3600
tgccatctag tgatgatgag gctactgctg actctcaaca ttctactcct ccaaaaaaga    3660
agagaaaggt agaagacccc aaggactttc cttcagaatt gctaagtttt ttgagtcatg    3720
ctgtgtttag taatagaact cttgcttgct ttgctatta caccacaaag gaaaaagctg    3780
cactgctata caagaaaatt atggaaaaat atttgatgta tagtgccttg actagagatc    3840
ataatcagcc ataccacatt tgtagaggtt tacttgctt taaaaaacct cccacacctc    3900
cccctgaacc tgaaacataa aatgaatgca attgttgttg ttaacttgtt tattgcagct    3960
tataatggtt acaaataaag caatagcatc acaaatttca caaataaagc attttttca    4020 ctgcattcta gttgtggttt gtccaaactc atcaatgtat cttatcatgt ctggatcatc    4080
ccgccatggt atcaacgcca tatttctatt tacagtaggg acctcttcgt tgtgtaggta    4140
ccgctgtatt cctagggaaa tagtagaggc accttgaact gtctgcatca gccatatagc    4200
ccccgctgtt cgacttacaa acacaggcac agtactgaca aacccataca cctcctctga    4260
aatacccata gttgctaggg ctgtctccga actcattaca ccctccaaag tcagagctgt    4320
aatttcgcca tcaagggcag cgagggcttc tccagataaa atagcttctg ccgagagtcc    4380
cgtaagggta gacacttcag ctaatccctc gatgaggtct actagaatag tcagtgcggc    4440
tcccattttg aaaattcact tacttgatca gcttcagaag atggcggagg gcctccaaca    4500
cagtaatttt cctcccgact cttaaaatag aaaatgtcaa gtcagttaag caggaagtgg    4560
actaactgac gcagctggcc gtgcgacatc ctcttttaat tagttgctag gcaacgccct    4620
```

-continued

```
ccagagggcg tgtggttttg caagaggaag caaaagcctc tccacccagg cctagaatgt   4680
ttccacccaa tcattactat gacaacagct gtttttttta gtattaagca gaggccgggg   4740
acccctgggc cggcccgctt actctggaga aaaagaagag aggcattgta gaggcttcca   4800
gaggcaactt gtcaaaacag gactgcttct atttctgtca cactgtctgg ccctgtcaca   4860
aggtccagca cctccatacc cccttttaata agcagtttgg gaacgggtgc gggtcttact   4920
ccgcccatcc cgcccctaac tccgcccagt tccgcccatt ctccgcccca tggctgacta   4980
atttttttta tttatgcaga ggccgaggcc gcctcggcct ctgagctatt ccagaagtag   5040
tgaggaggct ttttttggagg cctaggcttt tgcaaaagc taattcggcg taatctgctg    5100
cttgcaaaca aaaaaccac cgctaccagc ggtggtttgt ttgccggatc aagagctacc    5160 aactctttt ccgaaggtaa ctggcttcag cagagcgcag ataccaaata ctgtccttct    5220
agtgtagccg tagttaggcc accacttcaa gaactctgta gcaccgccta catacctcgc    5280
tctgctaatc ctgttaccag tggctgctgc cagtggcgat aagtcgtgtc ttaccgggtt    5340
ggactcaaga cgatagttac cggataaggc gcagcggtcg ggctgaacgg ggggttcgtg    5400
cacacagccc agcttggagc gaacgaccta caccgaactg agatacctac agcgtgagca    5460
ttgagaaagc gccacgcttc ccgaagggag aaaggcggac aggtatccgg taagcggcag    5520
ggtcggaaca ggagagcgca cgagggagct tccaggggga aacgcctggt atctttatag    5580
tcctgtcggg tttcgccacc tctgacttga gcgtcgattt ttgtgatgct cgtcaggggg    5640
gcggagccta tggaaaaacg ccagcaacgc aagctagctt ctagctagaa attgtaaacg    5700
ttaatatttt gttaaaattc gcgttaaatt tttgttaaat cagctcattt tttaaccaat    5760
aggccgaaat cggcaaaatc ccttataaat caaaagaata gcccgagata gggttgagtg    5820
ttgttccagt ttggaacaag agtccactat taaagaacgt ggactccaac gtcaaagggc    5880
gaaaaaccgt ctatcagggc gatggcccgcc cactacgtga accatcaccc aaatcaagtt    5940
ttttggggtc gaggtgccgt aaagcactaa atcggaaccc taagggagc cccgattta    6000 gagcttgacg gggaaagccg gcgaacgtgg cgagaaagga agggaagaaa gcgaaaggag    6060
cgggcgctag ggcgctggca agtgtagcgg tcacgctgcg cgtaaccacc acacccgccg    6120
cgcttaatgc gccgctacag ggcgcgtact atggttgctt tgacgagacc gtataacgtg    6180
ctttcctcgt tggaatcaga gcgggagcta acaggaggc cgattaaagg gattttagac    6240
aggaacggta cgccagctgg attaccaaag ggcctcgtga tacgcctatt tttataggtt    6300
aatgtcatga taataatggt ttcttagacg tcaggtggca cttttcgggg aaatgtgcgc    6360
ggaaccccta tttgtttatt tttctaaata cattcaaata tgtatccgct catgagacaa    6420
taaccctgat aaatgcttca ataatattga aaaggaaga gtatgagtat tcaacatttc    6480
cgtgtcgccc ttattccctt ttttgcggca ttttgccttc ctgttttgtgc tcacccagaa    6540 acgctggtga agtaaaaga tgctgaagat cagttgggtg cacgagtggg ttacatcgaa    6600
ctggatctca acagcggtaa gatccttgag agttttcgcc ccgaagaacg ttttccaatg    6660
atgagcactt taaagttcct gctatgtggc gcggtattat cccgtgttga cgccgggcaa    6720
gagcaactcg gtcgccgcat acactattct cagaatgact tggttgagta ctcaccagtc    6780
acagaaaagc atcttacgga tggcatgaca gtaagagaat tatgcagtgc tgccataacc    6840
atgagtgata acactgcggc caacttactt ctgacaacga tcggaggacc gaaggagcta    6900
accgcttttt tgcacaacat ggggatcat gtaactcgcc ttgatcgttg gaaccggag    6960 ctgaatgaag ccataccaaa cgacgagcgt gacaccacga tgcctgcagc aatggcaaca    7020
```

-continued

```
acgttgcgca aactattaac tggcgaacta cttactctag cttcccggca acaattaata   7080
gactggatgg aggcggataa agttgcagga ccacttctgc gctcggccct tccggctggc   7140
tggtttattg ctgataaatc tggagccggt gagcgtgggt ctcgcggtat cattgcagca   7200
ctggggccag atggtaagcc ctcccgtatc gtagttatct acacgacggg gagtcaggca   7260
actatggatg aacgaaatag acagatcgct gagataggtg cctcactgat taagcattgg   7320
taactgtcag accaagttta ctcatatata ctttagattg atttaaaact tcatttttaa   7380
tttctctagc gcgttgacat tgattattga ctagttatta atagtaatca attacggggt   7440
cattagttca tagcccatat atggagttcc gcgttacata acttacggta aatggcccgc   7500
ctggctgacc gcccaacgac ccccgcccat tgacgtcaat aatgacgtat gttcccatag   7560
taacgccaat agggactttc cattgacgtc aatgggtgga ctatttacgg taaactgccc   7620
acttggcagt acatcaagtg tatcatatgc caagtacgcc ccctattgac gtcaatgacg   7680
gtaaatggcc cgcctggcat tatgcccagt acatgacctt atgggacttt cctacttggc   7740
agtacatcta cgtattagtc atcgctatta ccatggtgat gcggttttgg cagtacatca   7800
atgggcgtgg atagcggttt gactcacggg gatttccaag tctccacccc attgacgtca   7860
atgggagttt gttttggcac caaaatcaac gggactttcc aaaatgtcgt aacaactccg   7920
ccccattgac gcaaatgggc ggtaggcgtg tacggtggga ggtctatata agcagagctc   7980
tctggctaac t
```